United States Patent
Liu et al.

(10) Patent No.: US 9,670,264 B2
(45) Date of Patent: Jun. 6, 2017

(54) WATER SOLUBLE G-PROTEIN COUPLED RECEPTOR

(71) Applicant: The Trustees of The University of Pennsylvania, Philadelphia, PA (US)

(72) Inventors: Renyu Liu, Media, PA (US); Jeffery G Saven, Philadelphia, PA (US); Jose Manuel Perez-Aguilar, New York, NY (US); Felipe Matsunaga, Olmsted Township, OH (US); Jin Xi, Media, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/786,578

(22) PCT Filed: Apr. 25, 2014

(86) PCT No.: PCT/US2014/035524
§ 371 (c)(1),
(2) Date: Oct. 23, 2015

(87) PCT Pub. No.: WO2014/176544
PCT Pub. Date: Oct. 30, 2014

(65) Prior Publication Data
US 2016/0102130 A1   Apr. 14, 2016

Related U.S. Application Data

(60) Provisional application No. 61/815,939, filed on Apr. 25, 2013.

(51) Int. Cl.
*A61K 38/00* (2006.01)
*C07K 14/705* (2006.01)
*G01N 33/74* (2006.01)
*G01N 33/566* (2006.01)

(52) U.S. Cl.
CPC ............ *C07K 14/705* (2013.01); *A61K 38/00* (2013.01); *G01N 33/566* (2013.01); *G01N 33/74* (2013.01); *C07K 2319/21* (2013.01); *C07K 2319/42* (2013.01); *G01N 2500/04* (2013.01)

(58) Field of Classification Search
None
See application file for complete search history.

(56) References Cited

U.S. PATENT DOCUMENTS

| | | | |
|---|---|---|---|
| 2011/0214189 A1* | 9/2011 | Gaitanaris | C07K 14/723 800/3 |
| 2012/0252719 A1* | 10/2012 | Zhang | C07K 14/705 514/1.7 |
| 2012/0270230 A1 | 10/2012 | Henderson et al. | |

OTHER PUBLICATIONS

Crasto, Hydrophobicity Profiles in G Protein-Coupled Receptor Transmembrane Helical Domains, J. Receptor Ligand Channel Res., 2010, vol. 3, 123-133.
Cui, et al., "NMR Structure and Dynamics of a Designed Water-Soluble Transmembrane Domain of Nicotinic Acetylcholine Receptor",Biochim Biophys Acta., 2012, vol. 1818(3), 617-626.
Ma, et al., "NMR Studies of a Channel Protein Without Membranes: Structure and Dynamics of Water-Solubilized KcsA", Proc Natl Acad Sci, 2008, vol. 105(43), 16537-42.
Perez-Aguilar, et al., "A Computationally Designed Water-Soluble Variant of a G-Protein-Coupled Receptor: The Human Mu Opioid Receptor. PLoS One", Jun. 2013, vol. 8(6), 1-10.
Slovic, et al., "Computational Design of a Water-Soluble Analog of Phospholamban", Protein Sci., 2003, vol. 12(2), 337-48.

* cited by examiner

*Primary Examiner* — John Ulm
(74) *Attorney, Agent, or Firm* — Baker & Hostetler LLP

(57) ABSTRACT

Described herein are recombinant integral membrane proteins having multiple transmembrane domains that have been engineered to be less hydrophobic, through alteration of the amino acid sequence of the native protein, but retain the ability to bind their natural ligand. The decreased hydrophobicity of the described proteins makes them more water soluble than the native protein, which allows the described proteins to be expressed in bacteria in large quantities and isolated in the absence of membranes, all while retaining the ability to interact with known ligands.

18 Claims, 14 Drawing Sheets

SEQUENCE LISTING

<160> NUMBER OF SEQ ID NOS: 15

<210> SEQ ID NO 1
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser Met Ile Thr Ala Ile Lys Ile His Glu Glu Tyr Lys Lys Val Cys
1               5                   10                  15

Glu Glu Gly Lys Lys Gly Asn Lys Leu Val Met Glu Val Ile Val Arg
            20                  25                  30

Tyr Thr Lys Met Lys Thr Ala Thr Asn Ile Tyr Ile Phe Asn Leu Ala
        35                  40                  45

Lys Ala Asp Ala Leu Ala Glu Ser Thr Leu Pro Phe Gln Ser Val Asn
    50                  55                  60

Lys Leu Met Gly Thr Trp Pro Phe Gly Thr Ile Leu Cys Lys Lys Val
65                  70                  75                  80

Ile Ser Ile Asp Tyr Tyr Asn Met Phe Thr Ser Ile Phe Thr Leu Cys
                85                  90                  95

Thr Met Ser Val Asp Arg Tyr Ile Ala Val Cys His Pro Val Lys Ala
            100                 105                 110

Leu Asp Phe Arg Thr Pro Arg Asn Ala Lys Glu Glu Asn Glu Lys Asn
        115                 120                 125

Trp Lys Leu Ser Ser Glu Ile Gly Lys Pro Val Glu Lys Lys Ala Thr
    130                 135                 140

Thr Lys Tyr Arg Gln Gly Ser Ile Asp Cys Thr Leu Thr Phe Ser His
145                 150                 155                 160

Pro Thr Trp Tyr Trp Glu Asp Lys Leu Lys Asp Glu Val Phe Lys Lys
                165                 170                 175

Ala Phe Glu Glu Pro Val Lys Lys Ile Lys Glu Cys Tyr Gly Leu Met
            180                 185                 190

Ile Leu Arg Leu Lys Ser Val Arg Met Leu Ser Gly Ser Lys Glu Lys
        195                 200                 205

Asp Arg Asn Leu Arg Arg Ile Thr Arg Met Val Leu Val Val Val Glu
    210                 215                 220

Val Phe Ile Lys Cys Trp Thr Glu Ile His Lys Tyr Val Lys Glu Gly
225                 230                 235                 240

Lys Leu Val Thr Ile Pro Glu Thr Thr Phe Gln Thr Val Ser Trp His
                245                 250                 255

Glu Cys Ile Ala Lys Gly Tyr Lys Asn Ser Cys Glu Asn Pro Lys Leu
            260                 265                 270

```
Tyr Glu Glu Leu Asp Glu Asn Phe Lys Arg Cys Phe Arg Glu Phe Cys
            275                 280                 285

<210> SEQ ID NO 2
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ser Met Ile Thr Ala Ile Lys Ile Leu Glu Glu Tyr Lys Lys Val Cys
1               5                   10                  15

Glu Glu Gly Arg Lys Gly Asn Lys Leu Val Met Glu Val Ile Val Arg
            20                  25                  30

Tyr Thr Lys Met Lys Thr Ala Thr Asn Ile Tyr Ile Phe Asn Leu Ala
        35                  40                  45

Lys Ala Asp Ala Leu Ala Glu Ser Thr Leu Pro Phe Gln Ser Val Asn
50                  55                  60

Lys Leu Met Gly Thr Trp Pro Phe Gly Thr Ile Leu Cys Lys Lys Val
65                  70                  75                  80

Ile Ser Ile Asp Tyr Tyr Asn Met Phe Thr Ser Ile Phe Thr Leu Cys
                85                  90                  95

Thr Met Ser Val Asp Arg Tyr Ile Ala Val Cys His Pro Val Lys Ala
            100                 105                 110

Leu Asp Phe Arg Thr Pro Arg Asn Ala Lys Glu His Asn Glu Lys Asn
        115                 120                 125

Trp Lys Leu Ser Ser Glu Ile Gly Lys Pro Val Glu Lys Arg Ala Thr
    130                 135                 140

Thr Lys Tyr Arg Gln Gly Ser Ile Asp Cys Thr Leu Thr Phe Ser His
145                 150                 155                 160

Pro Thr Trp Tyr Trp Glu Asp Lys Leu Lys Asp Thr Val Phe Lys Lys
                165                 170                 175

Ala Phe Glu Glu Pro Val Lys Val Ile Lys Glu Cys Tyr Gly Leu Met
            180                 185                 190

Ile Leu Arg Leu Lys Ser Val Arg Met Leu Ser Gly Ser Lys Glu Lys
        195                 200                 205

Asp Arg Asn Leu Arg Arg Ile Thr Arg Met Val Leu Val Val Val Glu
    210                 215                 220

Val Phe Ile Lys Cys Trp Thr Glu Ile His Lys Tyr Val Lys Glu Gly
225                 230                 235                 240

Lys Leu

<210> SEQ ID NO 3
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ser Glu Lys Lys Arg Glu Lys Ile Phe Gln Glu Tyr Lys Lys Val Tyr
1               5                   10                  15

Glu Glu Gly Lys Glu Gly Asn Lys Leu Val Val Asp Val Ile Glu Arg
            20                  25                  30
```

```
Tyr Thr Lys Met Lys Thr Ala Thr Asn Asp Tyr Ile Arg Asn Leu Ala
            35                  40                  45

Glu Ala Asp Met Lys Ala Thr Glu Thr Leu Pro Tyr Gln Ser Glu Asn
 50                  55                  60

Tyr Leu Lys Gly Thr Trp Pro Phe Gly Thr Glu Glu Cys Lys Lys Val
 65                  70                  75                  80

Ile Ser Gln Asp Tyr Tyr Asn Met Phe Thr Ser Ile Glu Thr Leu Lys
                 85                  90                  95

Thr Met Ser Glu Asp Arg Tyr Ile Ala Val Glu His Pro Val Lys Ala
            100                 105                 110

Leu Asp Phe Arg Thr Pro Arg Asp Ala Gln Glu Lys Asn Lys Glu Asn
            115                 120                 125

Trp Glu Lys Ser Lys Lys Ile Gly Glu Pro Val Glu Lys Ser Ala Thr
130                 135                 140

Thr Lys Tyr Arg Gln Gly Ser Ile Asp Cys Thr Leu Thr Phe Ser His
145                 150                 155                 160

Pro Thr Trp Tyr Trp Glu Asn Lys Gln Lys Lys Val Phe Glu Glu
                165                 170                 175

Ala Phe Lys Lys Pro Val Glu Glu Ile Lys Lys His Glu Glu Met
            180                 185                 190

Gln Lys Arg Leu Lys Ser Val Arg Met Leu Ser Gly Ser Lys Glu Lys
            195                 200                 205

Asp Arg Asn Leu Arg Arg Ile Thr Arg Met Val Met Glu Val Val Gln
            210                 215                 220

Val Phe Ile Lys His Trp Asp Pro Ile His Lys Tyr Val Lys Asp Lys
225                 230                 235                 240

Ala Glu Lys Thr Ile Pro Glu Thr Thr Phe Gln Thr Lys Lys Trp His
                245                 250                 255

Glu Ser Ile Ile Glu Gly Tyr Lys Asn Ser Asp His Asn Pro Lys Leu
            260                 265                 270

Tyr Asp Glu Asn Asp Glu Asn Phe Lys Arg His Phe Arg Glu Phe Lys
            275                 280                 285

<210> SEQ ID NO 4
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ser Glu Lys Lys Lys Glu Glu Ile Trp Lys Glu Tyr Lys Glu Trp Ile
 1               5                  10                  15

Glu Lys Gly Lys Lys Gly Asn Lys Leu Val Met Glu Val Ile Glu Arg
            20                  25                  30

Tyr Thr Lys Met Lys Thr Ala Thr Asn Asp Tyr Ile Lys Asn Leu Ala
            35                  40                  45

Glu Ala Asp Trp Lys Ala Thr Glu Thr Leu Pro Glu Gln Ser Lys Asn
 50                  55                  60

Tyr Leu Glu Gly Thr Trp Pro Phe Gly Lys Glu Lys Cys Lys Glu Val
 65                  70                  75                  80

Ile Ser Arg Asp Tyr Tyr Asn Met Phe Thr Ser Ile Tyr Thr Leu Lys
                 85                  90                  95

Thr Met Ser Lys Asp Arg Tyr Ile Ala Val Asp His Pro Val Lys Ala
            100                 105                 110
```

Leu Asp Phe Arg Thr Pro Arg Glu Ala Lys Lys Glu Asn Lys Lys Asn
        115                 120                 125

Trp Glu Glu Ser Lys Lys Ile Gly Glu Pro Val Lys Lys Asp Ala Thr
    130                 135                 140

Thr Lys Tyr Arg Gln Gly Ser Ile Asp Cys Thr Leu Thr Phe Ser His
145                 150                 155                 160

Pro Thr Trp Tyr Trp Glu Asn Lys Gln Lys Glu Glu Val Phe Lys Lys
                165                 170                 175

Ala Phe Glu Glu Pro Val Lys Asp Ile Glu Glu Gln Lys Lys Lys Met
            180                 185                 190

Asp Glu Arg Leu Lys Ser Val Arg Met Leu Ser Gly Ser Lys Glu Lys
            195                 200                 205

Asp Arg Asn Leu Arg Arg Ile Thr Arg Met Val Trp Glu Val Val Lys
        210                 215                 220

Lys Phe Phe Glu Lys Trp Lys Pro Ile His Glu Val Lys Lys Lys
225                 230                 235                 240

Ala Glu Lys Thr Ile Pro Glu Thr Thr Phe Gln Thr Glu Glu Trp His
            245                 250                 255

Lys Lys Ile Tyr Glu Gly Tyr Lys Asn Ser Glu Asn Pro Lys Leu
            260                 265                 270

Tyr Asp Glu Lys Asp Glu Asn Phe Lys Arg Glu Phe Arg Glu Phe Glu
        275                 280                 285

<210> SEQ ID NO 5
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ser Glu Glu Lys Lys Lys Ile Asp Glu Glu Tyr Lys Lys Gln Ile
1               5                   10                  15

Glu Glu Gly Lys Lys Gly Asn Lys Leu Val Glu Asp Val Ile Glu Arg
            20                  25                  30

Tyr Thr Lys Met Lys Thr Ala Thr Asn Ile Tyr Ile Lys Asn Leu Ala
        35                  40                  45

Gln Ala Asp Gln Gly Ala Thr Lys Thr Leu Pro Glu Gln Ser Lys Asn
    50                  55                  60

Tyr Leu Glu Gly Thr Trp Pro Phe Gly Lys Glu Lys Cys Lys Glu Val
65                  70                  75                  80

Ile Ser Lys Asp Tyr Tyr Asn Met Phe Thr Ser Ile Trp Thr Leu Asp
                85                  90                  95

Thr Met Ser Glu Asp Arg Tyr Ile Ala Val Glu His Pro Val Lys Ala
            100                 105                 110

Leu Asp Phe Arg Thr Pro Arg Lys Ala Lys Glu Glu Asn Lys Lys Asn
        115                 120                 125

Trp Glu Glu Ser Lys Lys Ile Gly Glu Pro Val Lys Lys Glu Ala Thr
    130                 135                 140

Thr Lys Tyr Arg Gln Gly Ser Ile Asp Cys Thr Leu Thr Phe Ser His
145                 150                 155                 160

Pro Thr Trp Tyr Trp Glu Asn Lys Trp Lys Glu Glu Val Phe Lys Lys
                165                 170                 175

Ala Phe Glu Glu Pro Val Lys Lys Ile Glu Glu Arg Lys Lys Lys Met

```
            180             185             190
Glu Glu Arg Leu Lys Ser Val Arg Met Leu Ser Gly Ser Lys Glu Lys
                195                 200                 205
Asp Arg Asn Leu Arg Arg Ile Thr Arg Met Val Glu Asn Val Val Lys
            210                 215                 220
Arg Phe Glu Glu His Trp Lys Pro Ile His Glu Arg Val Lys Glu Lys
225                 230                 235                 240
Ala Lys Lys Thr Ile Pro Glu Thr Thr Phe Gln Thr Glu Glu Trp His
                245                 250                 255
Lys Glu Ile Gln Lys Gly Tyr Glu Asn Ser Lys Glu Asn Pro Lys Leu
            260                 265                 270
Tyr Glu Lys Glu Asp Glu Asn Phe Lys Arg Glu Phe Arg Glu Phe Lys
                275                 280                 285

<210> SEQ ID NO 6
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ser Glu Glu Thr Ala Glu Glu Ile Glu Lys Gln Tyr Lys Val Glu Ile
1               5                   10                  15
Glu Lys Gly Lys Lys Gly Asn Lys Leu Val Lys Glu Val Ile Glu Arg
            20                  25                  30
Tyr Thr Lys Met Lys Thr Ala Thr Asn Ile Tyr Ile Trp Asn Leu Ala
        35                  40                  45
Glu Ala Asp Leu Lys Ala Thr Glu Thr Leu Pro Lys Gln Ser Gln Asn
    50                  55                  60
Tyr Leu Glu Gly Thr Trp Pro Phe Gly Gln Glu Asp Cys Lys Asn Val
65                  70                  75                  80
Ile Ser Ile Asp Tyr Tyr Asn Met Phe Thr Ser Ile Trp Thr Leu Ala
                85                  90                  95
Thr Met Ser Glu Asp Arg Tyr Ile Ala Val Ala His Pro Val Lys Ala
            100                 105                 110
Leu Asp Phe Arg Thr Pro Arg Glu Ala Glu Lys Glu Asn Lys Lys Asn
        115                 120                 125
Trp Glu Glu Ser Lys Lys Ile Gly Glu Pro Val Lys Lys Asp Ala Thr
130                 135                 140
Thr Lys Tyr Arg Gln Gly Ser Ile Asp Cys Thr Leu Thr Phe Ser His
145                 150                 155                 160
Pro Thr Trp Tyr Trp Glu Asn Asp Leu Lys Asp Val Phe Lys Lys
                165                 170                 175
Ala Phe Glu Glu Pro Val Lys Lys Ile Glu Glu Ala Tyr Lys Lys Met
            180                 185                 190
Gln Glu Arg Leu Lys Ser Val Arg Met Leu Ser Gly Ser Lys Glu Lys
        195                 200                 205
Asp Arg Asn Leu Arg Arg Ile Thr Arg Met Val Trp Lys Val Val Gln
    210                 215                 220
Ile Phe Ile Glu Ala Trp Asp Pro Ile His Lys Tyr Val Ile Glu Lys
225                 230                 235                 240
Ala Lys Glu Thr Ile Pro Glu Thr Thr Phe Gln Thr Glu Glu Trp His
                245                 250                 255
```

```
Lys Ser Ile Ala Glu Gly Tyr Lys Asn Ser Ala Glu Asn Pro Glu Leu
            260                 265                 270

Tyr Lys Lys Asp Asp Glu Asn Phe Lys Arg Thr Phe Arg Glu Phe Glu
        275                 280                 285

<210> SEQ ID NO 7
<211> LENGTH: 422
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ala His His His His His His Val Met Gly Gln Pro Gly Asn Gly
1               5                   10                  15

Ser Ala Phe Leu Leu Ala Pro Asn Gly Ser His Ala Pro Asp His Asp
            20                  25                  30

Val Thr Gln Gln Arg Asp Glu Glu Trp Val Lys Gly Gln Gly Lys Lys
        35                  40                  45

Met Ser Glu Ile Val Lys Lys Ile Val Glu Gly Asn Lys Leu Val Ile
50                  55                  60

Thr Ala Ile Lys Lys Phe Glu Arg Leu Gln Thr Val Thr Asn Tyr Phe
65                  70                  75                  80

Ile Thr Ser Leu Ala Glu Ala Asp Leu Lys Met Gly Glu Ala Val Val
            85                  90                  95

Pro Tyr Gly Ala Ala His Ile Leu Lys Lys Met Trp Thr Tyr Gly Asn
        100                 105                 110

Lys Trp Cys Glu Tyr Trp Thr Ser Ile Asp Val Leu Thr Val Thr Ala
        115                 120                 125

Ser Ile Glu Thr Leu Asp Val Ile Ala Glu Asp Arg Tyr Lys Ala Ile
    130                 135                 140

Thr Ser Pro Phe Lys Tyr Gln Ser Glu Leu Thr Lys Asn Lys Ala Arg
145                 150                 155                 160

Glu Glu Ile Lys Lys Val Trp Glu Arg Ser Gly Lys Thr Ser Phe Asp
                165                 170                 175

Pro Ile Gln Lys His Lys Tyr Arg Ala Thr His Gln Glu Ala Ile Asn
            180                 185                 190

Cys Tyr Ala Asn Glu Thr Cys Cys Asp Phe Phe Thr Asn Gln Asp Tyr
        195                 200                 205

Ala Lys Lys Ser Ser Lys Glu Ser Phe Tyr Glu Pro Leu Lys Lys Met
    210                 215                 220

Lys Glu Val Tyr Ser Arg Val Glu Gln Glu Ala Lys Arg Gln Leu Gln
225                 230                 235                 240

Lys Ile Asp Lys Ser Glu Gly Arg Phe His Val Gln Asn Leu Ser Gln
                245                 250                 255

Val Glu Gln Asp Gly Arg Thr Gly His Gly Leu Arg Arg Ser Ser Lys
            260                 265                 270

Glu Ser Leu Lys Glu His Lys Ala Leu Lys Thr Leu Gly Glu Ile Met
        275                 280                 285

Gly Thr Phe Thr Lys Gln Trp Glu Pro Phe Phe Lys Val Asn Glu Glu
    290                 295                 300

His Val Lys Gln Asp Asn Lys Ile Arg Lys Glu Glu Tyr Ile Lys Leu
305                 310                 315                 320

Asn Trp Glu Gly Tyr Lys Asn Ser Gly Glu Asn Pro Lys Ile Tyr Glu
                325                 330                 335
```

```
Arg Ser Pro Asp Phe Arg Ile Ala Phe Gln Glu Leu Lys Ser Leu Arg
            340                 345                 350

Arg Ser Ser Leu Lys Ala Tyr Gly Asn Gly Tyr Ser Ser Asn Gly Asn
            355                 360                 365

Thr Gly Glu Gln Ser Gly Tyr His Val Glu Gln Glu Lys Glu Asn Lys
370                 375                 380

Leu Leu Ala Glu Asp Leu Pro Gly Thr Glu Asp Phe Val Gly His Gln
385                 390                 395                 400

Gly Thr Val Pro Ser Asp Asn Ile Asp Ser Pro Gly Arg Asn Ala Ser
                405                 410                 415

Thr Asn Asp Ser Leu Leu
            420

<210> SEQ ID NO 8
<211> LENGTH: 422
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ala His His His His His Val Met Gly Gln Pro Gly Asn Gly
1               5                   10                  15

Ser Ala Phe Leu Leu Ala Pro Asn Gly Ser His Ala Pro Asp His Asp
                20                  25                  30

Val Thr Gln Gln Arg Asp Glu Glu Trp Val Lys Gly Thr Gly Arg Gln
            35                  40                  45

Met Ser Glu Ile Val Lys Lys Ile Val Glu Gly Asn Lys Leu Val Ile
    50                  55                  60

Thr Ala Ile Gln Lys Phe Glu Arg Leu Gln Thr Val Thr Asn Tyr Phe
65                  70                  75                  80

Ile Thr Ser Leu Ala Glu Ala Asp Leu Lys Met Gly Glu Ala Val Val
                85                  90                  95

Pro Tyr Gly Ala Ala His Ile Leu Lys Lys Met Trp Thr Tyr Gly Asn
            100                 105                 110

Arg Trp Cys Glu Tyr Trp Thr Ser Ile Asp Val Leu Thr Val Thr Ala
        115                 120                 125

Ser Ile Glu Thr Leu Asp Val Ile Ala Glu Asp Arg Tyr Lys Ala Ile
    130                 135                 140

Thr Ser Pro Phe Lys Tyr Gln Ser Glu Leu Thr Lys Asn Lys Ala Arg
145                 150                 155                 160

Glu Glu Ile Lys Lys Val Trp Glu Arg Ser Gly Lys Thr Ser Phe Asp
                165                 170                 175

Pro Ile Gln Lys His Lys Tyr Arg Ala Thr His Gln Glu Ala Ile Asn
            180                 185                 190

Cys Tyr Ala Asn Glu Thr Cys Cys Asp Phe Phe Thr Asn Gln Asp Tyr
        195                 200                 205

Ala Lys Lys Ser Ser Lys Gln Ser Phe Tyr Glu Pro Leu Gln Lys Met
    210                 215                 220

Lys Asp Val Tyr Ser Arg Val Glu Gln Glu Ala Lys Arg Gln Leu Gln
225                 230                 235                 240

Lys Ile Asp Lys Ser Glu Gly Arg Phe His Val Gln Asn Leu Ser Gln
                245                 250                 255

Val Glu Gln Asp Gly Arg Thr Gly His Gly Leu Arg Arg Ser Ser Lys
```

```
              260                 265                 270
Glu Ser Leu Lys Glu His Lys Ala Leu Lys Thr Leu Gly Glu Ile Met
            275                 280                 285

Gly Thr Phe Thr Arg Gln Trp Asp Pro Phe Lys Val Asn Glu Glu
        290                 295                 300

His Val Lys Gln Asp Asn Lys Ile Arg Lys Glu Tyr Ile Lys Leu
305                 310                 315                 320

Asn Trp Glu Gly Tyr Lys Asn Ser Gly Glu Asn Pro Lys Ile Tyr Glu
                325                 330                 335

Arg Ser Pro Asp Phe Arg Ile Ala Phe Gln Glu Leu Arg Ser Leu Arg
                340                 345                 350

Arg Ser Ser Leu Lys Ala Tyr Gly Asn Gly Tyr Ser Ser Asn Gly Asn
                355                 360                 365

Thr Gly Glu Gln Ser Gly Tyr His Val Glu Gln Glu Lys Glu Asn Lys
            370                 375                 380

Leu Leu Ala Glu Asp Leu Pro Gly Thr Glu Asp Phe Val Gly His Gln
385                 390                 395                 400

Gly Thr Val Pro Ser Asp Asn Ile Asp Ser Pro Gly Arg Asn Ala Ser
                405                 410                 415

Thr Asn Asp Ser Leu Leu
            420

<210> SEQ ID NO 9
<211> LENGTH: 288
<212> TYPE: PRT
<213> ORGANISM: Homo sapiens

<400> SEQUENCE: 9

Ser Met Ile Thr Ala Ile Thr Ile Met Ala Leu Tyr Ser Ile Val Cys
1               5                   10                  15

Val Val Gly Leu Phe Gly Asn Phe Leu Val Met Tyr Val Ile Val Arg
            20                  25                  30

Tyr Thr Lys Met Lys Thr Ala Thr Asn Ile Tyr Ile Phe Asn Leu Ala
        35                  40                  45

Leu Ala Asp Ala Leu Ala Thr Ser Thr Leu Pro Phe Gln Ser Val Asn
    50                  55                  60

Tyr Leu Met Gly Thr Trp Pro Phe Gly Thr Ile Leu Cys Lys Ile Val
65                  70                  75                  80

Ile Ser Ile Asp Tyr Tyr Asn Met Phe Thr Ser Ile Phe Thr Leu Cys
                85                  90                  95

Thr Met Ser Val Asp Arg Tyr Ile Ala Val Cys His Pro Val Lys Ala
            100                 105                 110

Leu Asp Phe Arg Thr Pro Arg Asn Ala Lys Ile Ile Asn Val Cys Asn
        115                 120                 125

Trp Ile Leu Ser Ser Ala Ile Gly Leu Pro Val Met Phe Met Ala Thr
    130                 135                 140

Thr Lys Tyr Arg Gln Gly Ser Ile Asp Cys Thr Leu Thr Phe Ser His
145                 150                 155                 160

Pro Thr Trp Tyr Trp Glu Asn Leu Leu Lys Ile Cys Val Phe Ile Phe
                165                 170                 175

Ala Phe Ile Met Pro Val Leu Ile Ile Thr Val Cys Tyr Gly Leu Met
            180                 185                 190

Ile Leu Arg Leu Lys Ser Val Arg Met Leu Ser Gly Ser Lys Glu Lys
        195                 200                 205
```

```
Asp Arg Asn Leu Arg Arg Ile Thr Arg Met Val Leu Val Val Val Ala
    210                 215                 220
Val Phe Ile Val Cys Trp Thr Pro Ile His Ile Tyr Val Ile Ile Lys
225                 230                 235                 240
Ala Leu Val Thr Ile Pro Glu Thr Thr Phe Gln Thr Val Ser Trp His
                245                 250                 255
Phe Cys Ile Ala Leu Gly Tyr Thr Asn Ser Cys Leu Asn Pro Val Leu
            260                 265                 270
Tyr Ala Phe Leu Asp Glu Asn Phe Lys Arg Cys Phe Arg Glu Phe Cys
        275                 280                 285

<210> SEQ ID NO 10
<211> LENGTH: 6
<212> TYPE: PRT
<213> ORGANISM: Mus sp.

<400> SEQUENCE: 10

Met Leu Ser Gly Ser Lys
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 11

His His His His His
1               5

<210> SEQ ID NO 12
<211> LENGTH: 16
<212> TYPE: PRT
<213> ORGANISM: Unknown
<220> FEATURE:
<223> OTHER INFORMATION: Description of Unknown: bovine rhodopsin
      peptide

<400> SEQUENCE: 12

Ser Leu Val Val Leu Ala Ile Glu Arg Tyr Val Val Val Cys Lys Pro
1               5                   10                  15

<210> SEQ ID NO 13
<211> LENGTH: 16
<212> TYPE: PRT
<213> ORGANISM: Unknown
<220> FEATURE:
<223> OTHER INFORMATION: Description of Unknown: beta-2 adrenergic
      receptor peptide

<400> SEQUENCE: 13

Thr Leu Cys Val Ile Ala Val Asp Arg Tyr Phe Ala Ile Thr Ser Pro
1               5                   10                  15

<210> SEQ ID NO 14
<211> LENGTH: 16
<212> TYPE: PRT
<213> ORGANISM: Unknown
<220> FEATURE:
<223> OTHER INFORMATION: Description of Unknown: MUR peptide

<400> SEQUENCE: 14

Thr Leu Cys Thr Met Ser Val Asp Arg Tyr Ile Ala Val Cys His Pro
```

```
<210> SEQ ID NO 15
<211> LENGTH: 288
<212> TYPE: PRT
<213> ORGANISM: Mus sp.

<400> SEQUENCE: 15

Met Val Thr Ala Ile Thr Ile Met Ala Leu Tyr Ser Ile Val Cys Val
1               5                   10                  15

Val Gly Leu Phe Gly Asn Phe Leu Val Met Tyr Val Ile Val Arg Tyr
                20                  25                  30

Thr Lys Met Lys Thr Ala Thr Asn Ile Tyr Ile Phe Asn Leu Ala Leu
            35                  40                  45

Ala Asp Ala Leu Ala Thr Ser Thr Leu Pro Phe Gln Ser Val Asn Tyr
        50                  55                  60

Leu Met Gly Thr Trp Pro Phe Gly Asn Ile Leu Cys Lys Ile Val Ile
65                  70                  75                  80

Ser Ile Asp Tyr Tyr Asn Met Phe Thr Ser Ile Phe Thr Leu Cys Thr
                85                  90                  95

Met Ser Val Asp Arg Tyr Ile Ala Val Cys His Pro Val Lys Ala Leu
                100                 105                 110

Asp Phe Arg Thr Pro Arg Asn Ala Lys Ile Val Asn Val Cys Asn Trp
            115                 120                 125

Ile Leu Ser Ser Ala Ile Gly Leu Pro Val Met Phe Met Ala Thr Thr
130                 135                 140

Lys Tyr Arg Gln Gly Ser Ile Asp Cys Thr Leu Thr Phe Ser His Pro
145                 150                 155                 160

Thr Trp Tyr Trp Glu Asn Leu Leu Lys Ile Cys Val Phe Ile Phe Ala
                165                 170                 175

Phe Ile Met Pro Val Leu Ile Ile Thr Val Cys Tyr Gly Leu Met Ile
                180                 185                 190

Leu Arg Leu Lys Ser Val Arg Met Leu Ser Gly Ser Lys Glu Lys Asp
            195                 200                 205

Arg Asn Leu Arg Arg Ile Thr Arg Met Val Leu Val Val Val Ala Val
            210                 215                 220

Phe Ile Val Cys Trp Thr Pro Ile His Ile Tyr Val Ile Ile Lys Ala
225                 230                 235                 240

Leu Ile Thr Ile Pro Glu Thr Thr Phe Gln Thr Val Ser Trp His Phe
                245                 250                 255

Cys Ile Ala Leu Gly Tyr Thr Asn Ser Cys Leu Asn Pro Val Leu Tyr
                260                 265                 270

Ala Phe Leu Asp Glu Asn Phe Lys Arg Cys Phe Arg Glu Phe Cys Ile
            275                 280                 285
```

WATER SOLUBLE G-PROTEIN COUPLED RECEPTOR

CROSS-REFERENCE TO RELATED APPLICATIONS

This application is a National Stage Application filed under 35 U.S.C. 371 of International Application No. PCT/US2014/035524, filed Apr. 25, 2014, which claims the benefit of U.S. Provisional Patent Application 61/815,939 filed Apr. 25, 2013, each of which applications is incorporated herein by reference in its entirety for any and all purposes.

GOVERNMENT RIGHTS

The subject matter disclosed herein was made with government support under K08-GM-093115-01 awarded by the National Institutes of Health, and DMR-0425780, DMR08-32802, and DMR-1120901, which were awarded by the National Science Foundation. The Government has certain rights in the herein disclosed subject matter.

TECHNICAL FIELD

Described herein are recombinant, water soluble variants of membrane-spanning G-protein coupled receptors that may be expressed and isolated from bacteria in a manner that retains properties of the protein related to its functionality.

BACKGROUND

The G-protein-coupled receptor (GPCR) family of proteins have important roles in signal transduction and cellular response to extracellular stimuli. For this reason GPCRs are the target of many pharmaceuticals. The μ opioid receptor (MUR) is a GPCR that is the dominant target of opioids, many of which are potent analgesics widely used for the treatment of severe and chronic pain, e.g., morphine. Opioid use has soared in recent years and human MUR has been linked to abuse and many notorious side effects, including addiction and deadly respiratory depression.

The molecular mechanisms governing GPCR function remains obscure despite the profound insights obtained recently from multiple high-resolution crystal structures. Drug development and the study of the molecular mechanisms of GPCRs are impeded by limited solubility and difficulty in isolating sufficient quantities of functional receptors. These difficulties are caused in part by the large numbers of hydrophobic residues on the transmembrane, lipid-contacting protein exterior. Functional studies of MUR, and other GPCRs, could be carried out or greatly accelerated if forms of the protein existed that are water soluble, retain properties of native protein functionality, and are easily obtained in large quantity.

SUMMARY

Described herein are recombinant integral membrane proteins having multiple transmembrane domains computationally redesigned to increase their water solubility while retaining functionally related properties. The design involves several key steps: Comparative modeling using sequence alignment and known GPCR structures (the subsequently solved structure of murine MUR provided a means to assess the quality of the comparative model); Identification and computational redesign of transmembrane exterior residues; Overexpression in E. coli and purification; Characterization of structural and ligand-binding properties in aqueous buffer. The designed water-soluble human MUR has structurally and functionally related properties comparable to the native membrane-soluble human MUR.

DETAILED DESCRIPTION OF ILLUSTRATIVE EMBODIMENTS

Figure 1:
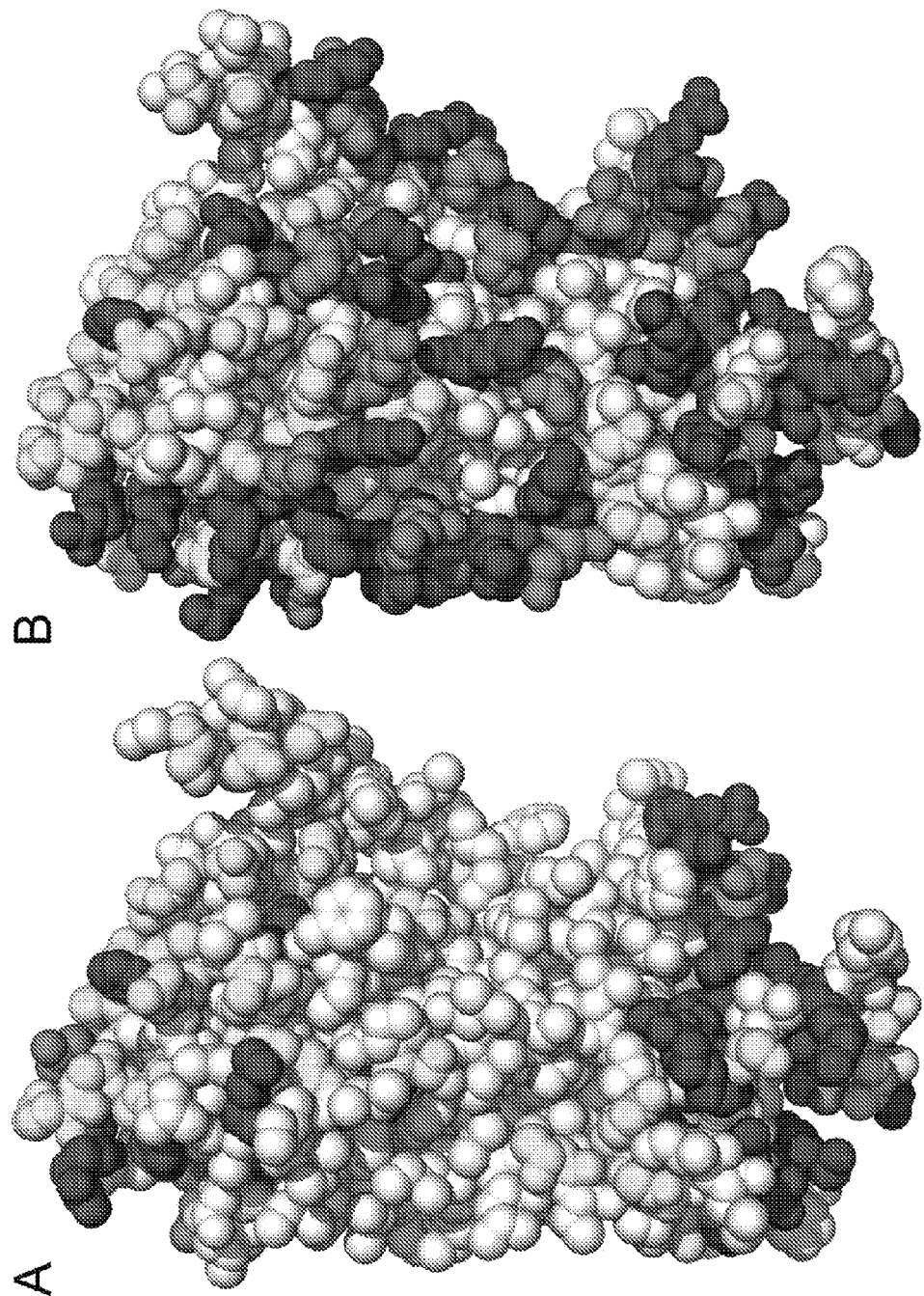
FIG. 1. Model structure of the human μ opioid receptor transmembrane domain used during the computational design. (A) Comparative model structure of the transmembrane domain of the native human μ opioid receptor. (B) Model of the computationally designed transmembrane-only water-soluble variant (wsMUR-TM) of the human μ opioid receptor. Residues are colored by amino acid types: hydrophilic in gray (GNQSTY); hydrophobic in white (ACFILMPVW); basic in dark gray (HKR); and acidic in dark gray (DE).

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of up to ±10% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about."

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

"Isolated" means altered "by the hand of man" from the natural state. If a molecule or composition occurs in nature, it has been "isolated" if it has been changed or removed from its original environment, or both. For example, a polynucleotide or a polypeptide naturally present in a living plant or animal is not "isolated," but the same polynucleotide or polypeptide separated from the coexisting materials of its natural state is "isolated" as the term is employed herein.

"Polynucleotide," synonymously referred to as "nucleic acid molecule" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

A "vector" is a replicon, such as plasmid, phage, cosmid, or virus in which another nucleic acid segment may be operably inserted so as to bring about the replication or expression of the segment.

A cell has been "transformed" when exogenous or heterologous nucleic acids such as DNA have been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell, or "stable cell" is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations. In some examples provided herein, cells are transformed by transfecting the cells with DNA.

The embodiments described herein are not limited to particular methods, reagents, compounds, compositions or biological systems, which can, of course, vary. Furthermore, the terminology used herein is for the purpose of describing particular antibodies or antigen-binding fragments only, and is not intended to be limiting.

Described herein are recombinant integral membrane proteins having multiple transmembrane domains that have been engineered to be less hydrophobic, through alteration of the amino acid sequence of the native protein, but retain the ability to bind their natural ligand. The decreased hydrophobicity of the described proteins makes them more water soluble than the native protein, which allows the described proteins to be expressed in bacteria in large quantities, and isolated in the absence of membranes, all while retaining the ability to interact with known ligands in the manner of the corresponding membrane protein.

In some embodiments the described recombinant integral membrane proteins have seven transmembrane domains, with 4 of these transmembrane domains each having at least 3 amino acid mutations that decrease the overall hydrophobicity of the recombinant integral membrane protein relative to the native protein. In another embodiment, the described recombinant integral membrane proteins having seven transmembrane domains, with at least 5 of these transmembrane domains each having at least 3 amino acid mutations that decrease the overall hydrophobicity of the recombinant integral membrane protein relative to the native protein. In some embodiments, the described recombinant integral membrane proteins are variants of a native protein characterized as a G-protein coupled receptor. For example, in some embodiments the described protein may be a recombinant form of a human mu opioid receptor. In another embodiment the described protein may be a recombinant form of a human $\beta_2$ adrenergic receptor.

In one embodiment, the described recombinant integral membrane protein has an amino acid sequence that is about 95% identical to that of SEQ ID NO: 1. In one embodiment, the described recombinant integral membrane protein has an amino acid sequence that is about 96% identical to that of SEQ ID NO: 1. In one embodiment, the described recombinant integral membrane protein has an amino acid sequence that is about 97% identical to that of SEQ ID NO: 1. In one embodiment, the described recombinant integral membrane protein has an amino acid sequence that is about 98% identical to that of SEQ ID NO: 1. In one embodiment, the described recombinant integral membrane protein has an amino acid sequence that is about 99% identical to that of SEQ ID NO: 1. In one embodiment, the described recombinant integral membrane protein has the amino acid sequence of SEQ ID NO: 1.

In one embodiment, the described recombinant integral membrane protein has an amino acid sequence that is about 95% identical to that of SEQ ID NO: 2. In one embodiment, the described recombinant integral membrane protein has an amino acid sequence that is about 96% identical to that of SEQ ID NO: 2. In one embodiment, the described recombinant integral membrane protein has an amino acid sequence that is about 97% identical to that of SEQ ID NO: 2. In one embodiment, the described recombinant integral membrane protein has an amino acid sequence that is about 98% identical to that of SEQ ID NO: 2. In one embodiment, the described recombinant integral membrane protein has an amino acid sequence that is about 99% identical to that of SEQ ID NO: 2. In one embodiment, the described recombinant integral membrane protein has the amino acid sequence of SEQ ID NO: 2.

In one embodiment, the described recombinant integral membrane protein has an amino acid sequence that is about 95% identical to that of SEQ ID NO: 3. In one embodiment, the described recombinant integral membrane protein has an amino acid sequence that is about 96% identical to that of SEQ ID NO: 3. In one embodiment, the described recombinant integral membrane protein has an amino acid sequence that is about 97% identical to that of SEQ ID NO: 3. In one embodiment, the described recombinant integral membrane protein has an amino acid sequence that is about 98% identical to that of SEQ ID NO: 3. In one embodiment, the described recombinant integral membrane protein has an amino acid sequence that is about 99% identical to that of SEQ ID NO: 3. In one embodiment, the described recombinant integral membrane protein has the amino acid sequence of SEQ ID NO: 3.

In one embodiment, the described recombinant integral membrane protein has an amino acid sequence that is about 95% identical to that of SEQ ID NO: 4. In one embodiment, the described recombinant integral membrane protein has an amino acid sequence that is about 96% identical to that of SEQ ID NO: 4. In one embodiment, the described recombinant integral membrane protein has an amino acid sequence that is about 97% identical to that of SEQ ID NO: 4. In one embodiment, the described recombinant integral membrane protein has an amino acid sequence that is about 98% identical to that of SEQ ID NO: 4. In one embodiment, the described recombinant integral membrane protein has an amino acid sequence that is about 99% identical to that of SEQ ID NO: 4. In one embodiment, the described recombinant integral membrane protein has the amino acid sequence of SEQ ID NO: 4.

In one embodiment, the described recombinant integral membrane protein has an amino acid sequence that is about 95% identical to that of SEQ ID NO: 5. In one embodiment, the described recombinant integral membrane protein has an amino acid sequence that is about 96% identical to that of SEQ ID NO: 5. In one embodiment, the described recombinant integral membrane protein has an amino acid sequence that is about 97% identical to that of SEQ ID NO: 5. In one embodiment, the described recombinant integral membrane protein has an amino acid sequence that is about 98% identical to that of SEQ ID NO: 5. In one embodiment, the described recombinant integral membrane protein has an amino acid sequence that is about 99% identical to that of SEQ ID NO: 5. In one embodiment, the described recombinant integral membrane protein has the amino acid sequence of SEQ ID NO: 5.

In one embodiment, the described recombinant integral membrane protein has an amino acid sequence that is about 95% identical to that of SEQ ID NO: 6. In one embodiment, the described recombinant integral membrane protein has an amino acid sequence that is about 96% identical to that of SEQ ID NO: 6. In one embodiment, the described recombinant integral membrane protein has an amino acid sequence that is about 97% identical to that of SEQ ID NO: 6. In one embodiment, the described recombinant integral membrane protein has an amino acid sequence that is about 98% identical to that of SEQ ID NO: 6. In one embodiment, the described recombinant integral membrane protein has an amino acid sequence that is about 99% identical to that of SEQ ID NO: 6. In one embodiment, the described recombinant integral membrane protein has the amino acid sequence of SEQ ID NO: 6.

In one embodiment, the described recombinant integral membrane protein has an amino acid sequence that is about 95% identical to that of SEQ ID NO: 7. In one embodiment, the described recombinant integral membrane protein has an amino acid sequence that is about 96% identical to that of SEQ ID NO: 7. In one embodiment, the described recombinant integral membrane protein has an amino acid sequence that is about 97% identical to that of SEQ ID NO: 7. In one embodiment, the described recombinant integral membrane protein has an amino acid sequence that is about 98% identical to that of SEQ ID NO: 7. In one embodiment, the described recombinant integral membrane protein has an amino acid sequence that is about 99% identical to that of SEQ ID NO: 7. In one embodiment, the described recombinant integral membrane protein has the amino acid sequence of SEQ ID NO: 7.

In one embodiment, the described recombinant integral membrane protein has an amino acid sequence that is about 95% identical to that of SEQ ID NO: 8. In one embodiment, the described recombinant integral membrane protein has an amino acid sequence that is about 96% identical to that of SEQ ID NO: 8. In one embodiment, the described recombinant integral membrane protein has an amino acid sequence that is about 97% identical to that of SEQ ID NO: 8. In one embodiment, the described recombinant integral membrane protein has an amino acid sequence that is about 98% identical to that of SEQ ID NO: 8. In one embodiment, the described recombinant integral membrane protein has an amino acid sequence that is about 99% identical to that of SEQ ID NO: 8. In one embodiment, the described recombinant integral membrane protein has the amino acid sequence of SEQ ID NO: 8.

| SEQ ID NO. | Construct Name | Amino Acid Sequence (excluding signal sequence) |
|---|---|---|
| 1 | wsMur-TM | SMITAIKIHEEYKKVCEEGKKGNKLVMEVIVRYTKMKTATNIYIFNLAKADALAESTLPFQSVNKLMGTWPFGTILCKKVISIDYYNMFTSIFTLCTMSVDRYIAVCHPVKALDFRTPRNAKEENEKNWKLSSEIGKPVEKKATTKYRQGSIDCTLTFSHPTWYWEDKLKDEVFKKAFEEPVKKIKECYGLMILRLKSVRMLSGSKEKDRNLRRITRMVLVVVEVFIKCWTEIHKYVKEGKLVTIPETTFQTVSWHECIAKGYKNSCENPKLYEELDENFKRCFREFC |
| 2 | wsMUR-TM + 7mut | SMITAIKILEEYKKVCEEGRKGNKLVMEVIVRYTKMKTATNIYIFNLAKADALAESTLPFQSVNKLMGTWPFGTILCKKVISIDYYNMFTSIFTLCTMSVDRYIAVCHPVKALDFRTPRNAKEHNEKNWKLSSEIGKPVEKRATTKYRQGSIDCTLTFSHPTWYWEDKLKDTVFKKAFEEPVKVIKECYGLMILRLKSVRMLSGSKEKDRNLRRITRMVLVVVEVFIKCWTEIHKYVKEGKL |
| 3 | G-min | SEKKREKIFQEYKKVYEEGKEGNKLVVDVIERYTKMKTATNDYIRNLAEADMKATETLPYQSENYLKGTWPFGTEECKKVISQDYYNMFTSIETLKTMSEDRYIAVEHPVKALDFRTPRDAQEKNKENWEKSKKIGEPVEKSATTKYRQGSIDCTLTFSHPTWYWENKQKQKVFEEAFKKPVEEIKKKHEEMQKRLKSVRMLSGSKEKDRNLRRITRMVMEVVQVFIKHWDPIHKYVKDKAEKTIPETTFQTKKWHESIIEGYKNSDHNPKLYDENDENFKRHFREFK |
| 4 | H-min | SEKKKEEIWKEYKEWIEKGKKGNKLVMEVIERYTKMKTATNDYIKNLAEADWKATETLPEQSKNYLEGTWPFGKEKCKEVISRDYYNMFTSIYTLKTMSKDRYIAVDHPVKALDFRTPREAKKENKKNWEESKKIGEPVKKDATTKYRQGSIDCTLTFSHPTWYWENKQKEEVFKKAFEEPVKDIEEQKKKMDERLKSVRMLSGSKEKDRNLRRITRMVWEVVKKFFEKWKPIHEEVKKKAEKTIPETTFQTEEWHKKIYEGYKNSEENPKLYDEKDENFKREFREFE |
| 5 | I-min | SEEKKKKIDEEYKKQIEEGKKGNKLVEDVIERYTKMKTATNIYIKNLAQADQGATKTLPEQSKNYLEGTWPFGKEKCKEVISKDYYNMFTSIWTLDTMSEDRYIAVEHPVKALDFRTPRKAKEENKKNWEESKKIGEPVKKEATTKYRQGSIDCTLTFSHPTWYWENKWKEEVFKKAFEEPVKKIEERKKKMEERLKSVRMLSGSKEKDRNLRRITRMVENVVKRFEEHWKPIHERVKEKAKKTIPETTFQTEEWHKEIQKGYENSKENPKLYEKEDENFKREFREFK |
| 6 | D-min | SEETAEEIEKQYKEVIEKGKKGNKLVKEVIERYTKMKTATNIYIWNLAEADLKATETLPKQSQNYLEGTWPFGQEDCKNVISIDYYNMFTSIWTLATMSEDRYIAVAHPVKALDFRTPREABKENKKNWEESKKIGEPVKKDATTKYRQGSIDCTLTFSHPTWYWENDLKDDVFKKAFEEPVKKIEEAYKKMQERLKSVRMLSGSKEKDRNLRRITRMVWKVVQIFIEAWDPIHKYVIEKAKETIPETTFQTEEWHKSIAEGYKNSAENPELYKKDDENFKRTFREFE |
| 7 | BAD3 | MAHHHHHHVMGQPGNGSAFLLAPNGSHAPDHDVTQQRDEEWVKGQGKKMSEIVKKIVEGNKLVITAIKKFERLQTVTNYFITSLAEADLKMGEAVVPYGAAHILKKMWTYGNKWCEYWTSIDVLTVTASIETLDVIAEDRYKAITSPFKYQSELTKNKAREEIKKVWERSGKTSFDPIQKHYRATHQEAINCYANETCCDFFTNQDYAKKSSKESFYEPLKKMKEVYSRVEQEAKRQLQKIDKSEGRFHVQNLSQVEQDGRTGHGLRRSSKESLKEHKALKTLGEIMGTFTKQWEPFFKVNEEHVKQDNKIRKEEYIKLNWEGYKNSGENPKIYERSPDFRIAFQELKSLRRSSLKAYGNGYSSNGNTGEQSGYHVEQEKENKLLAEDLPGTEDFVGHQGTVPSDNIDSPGRNASTNDSLL |
| 8 | BAD4 | MAHHHHHHVMGQPGNGSAFLLAPNGSHAPDHDVTQQRDEEWVKGTGRQMSEIVKKIVEGNKLVITAIQKFERLQTVTNYFITSLAEADLKMGEAVVPYGAAHILKKMWTYGNRWCEYWTSIDVLTVTASIETLDVIAEDRYKAITSPFKYQSELTKNKAREEIKKVWERSGKTSFDPIQKHYRATHQEAINCYANETCCDFFTNQDYAKKSSKQSFYEPLQKMKDVYSRVEQEAKRQLQKIDKSEGRFHVQNLSQVEQDGRTGHGLRRSSKESLKEHKALKTLGEIMGTFTRQWDPFFKVNEEHVKQDNKIRKEEYIKLNWEGYKNSGENPKIYERSPDFRIAFQELRSLRRSSLKAYGNGYSSNGNTGEQSGYHVEQEKENKLLAEDLPGTEDFVGHQGTVPSDNIDSPGRNASTNDSLL |
| 9 | Native MUR-TM | SMITAITIMALYSIVCVVGLFGNFLVMYVIVRYTKMKTATNIYIFNLALADALATSTLPFQSVNYLMGTWPFGTILCKIVISIDYYNMFTSIFTLCTMSVDRYIAVCHPVKALDFRTPRNAKIINVCNWILSSAIGLPVMFMATTKYRQGSIDCTLTFSHPTWYWENLLKICVFIFAFIMPVLIITVCYGLMILRLKSVRMLSGSKEKDRNLRRITRMVLVVVAVFIVCWTPIHIYVIIKALVTIPETTFQTVSWHFCIALGYTNSCLNPVLYAFLDENFKRCFREFC |

In some aspects the described recombinant integral membrane proteins can be further modified to have additional sequences present such as a signal sequence or an epitope tag to allow for selective binding or purification of the protein without the need to contact structural epitopes of the variant protein. As discussed herein, the epitope tag may be a polyhistidine tag or an HA epitope tag. In some embodiments the polyhistidine tag will include at least 5 consecutive histidine amino acid residues.

Polynucleotides encoding the described nucleotide sequences are also within the scope of the subject matter described herein. A polynucleotide encoding any one of the amino acid sequences for the described recombinant integral membrane proteins is provided. In one embodiment the described polynucleotide encodes a recombinant integral membrane protein having an amino acid sequence that is about 95% identical to that of SEQ ID NO: 1. In one embodiment the described polynucleotide encodes a recombinant integral membrane protein having an amino acid sequence that is about 96% identical to that of SEQ ID NO: 1. In one embodiment the described polynucleotide encodes a recombinant integral membrane protein having an amino acid sequence that is about 97% identical to that of SEQ ID NO: 1. In one embodiment the described polynucleotide encodes a recombinant integral membrane protein having an amino acid sequence that is about 98% identical to that of SEQ ID NO: 1. In one embodiment the described polynucleotide encodes a recombinant integral membrane protein having an amino acid sequence that is about 99% identical to that of SEQ ID NO: 1. In one embodiment the described polynucleotide encodes a recombinant integral membrane protein having the amino acid sequence of SEQ ID NO: 1.

In one embodiment the described polynucleotide encodes a recombinant integral membrane protein having an amino acid sequence that is about 95% identical to that of SEQ ID NO: 2. In one embodiment the described polynucleotide encodes a recombinant integral membrane protein having an amino acid sequence that is about 96% identical to that of SEQ ID NO: 2. In one embodiment the described polynucleotide encodes a recombinant integral membrane protein having an amino acid sequence that is about 97% identical to that of SEQ ID NO: 2. In one embodiment the described polynucleotide encodes a recombinant integral membrane protein having an amino acid sequence that is about 98% identical to that of SEQ ID NO: 2. In one embodiment the described polynucleotide encodes a recombinant integral membrane protein having an amino acid sequence that is about 99% identical to that of SEQ ID NO: 2. In one embodiment the described polynucleotide encodes a recombinant integral membrane protein having the amino acid sequence of SEQ ID NO: 2.

In one embodiment the described polynucleotide encodes a recombinant integral membrane protein having an amino acid sequence that is about 95% identical to that of SEQ ID NO: 3. In one embodiment the described polynucleotide encodes a recombinant integral membrane protein having an amino acid sequence that is about 96% identical to that of SEQ ID NO: 3. In one embodiment the described polynucleotide encodes a recombinant integral membrane protein having an amino acid sequence that is about 97% identical to that of SEQ ID NO: 3. In one embodiment the described polynucleotide encodes a recombinant integral membrane protein having an amino acid sequence that is about 98% identical to that of SEQ ID NO: 3. In one embodiment the described polynucleotide encodes a recombinant integral membrane protein having an amino acid sequence that is about 99% identical to that of SEQ ID NO: 3. In one embodiment the described polynucleotide encodes a recombinant integral membrane protein having the amino acid sequence of SEQ ID NO: 3.

In one embodiment the described polynucleotide encodes a recombinant integral membrane protein having an amino acid sequence that is about 95% identical to that of SEQ ID NO: 4. In one embodiment the described polynucleotide encodes a recombinant integral membrane protein having an amino acid sequence that is about 96% identical to that of SEQ ID NO: 4. In one embodiment the described polynucleotide encodes a recombinant integral membrane protein having an amino acid sequence that is about 97% identical to that of SEQ ID NO: 4. In one embodiment the described polynucleotide encodes a recombinant integral membrane protein having an amino acid sequence that is about 98% identical to that of SEQ ID NO: 4. In one embodiment the described polynucleotide encodes a recombinant integral membrane protein having an amino acid sequence that is about 99% identical to that of SEQ ID NO: 4. In one embodiment the described polynucleotide encodes a recombinant integral membrane protein having the amino acid sequence of SEQ ID NO: 4.

In one embodiment the described polynucleotide encodes a recombinant integral membrane protein having an amino acid sequence that is about 95% identical to that of SEQ ID NO: 5. In one embodiment the described polynucleotide encodes a recombinant integral membrane protein having an amino acid sequence that is about 96% identical to that of SEQ ID NO: 5. In one embodiment the described polynucleotide encodes a recombinant integral membrane protein having an amino acid sequence that is about 97% identical to that of SEQ ID NO: 5. In one embodiment the described polynucleotide encodes a recombinant integral membrane protein having an amino acid sequence that is about 98% identical to that of SEQ ID NO: 5. In one embodiment the described polynucleotide encodes a recombinant integral membrane protein having an amino acid sequence that is about 99% identical to that of SEQ ID NO: 5. In one embodiment the described polynucleotide encodes a recombinant integral membrane protein having the amino acid sequence of SEQ ID NO: 5.

In one embodiment the described polynucleotide encodes a recombinant integral membrane protein having an amino acid sequence that is about 95% identical to that of SEQ ID NO: 6. In one embodiment the described polynucleotide encodes a recombinant integral membrane protein having an amino acid sequence that is about 96% identical to that of SEQ ID NO: 6. In one embodiment the described polynucleotide encodes a recombinant integral membrane protein having an amino acid sequence that is about 97% identical to that of SEQ ID NO: 6. In one embodiment the described polynucleotide encodes a recombinant integral membrane protein having an amino acid sequence that is about 98% identical to that of SEQ ID NO: 6. In one embodiment the described polynucleotide encodes a recombinant integral membrane protein having an amino acid sequence that is about 99% identical to that of SEQ ID NO: 6. In one embodiment the described polynucleotide encodes a recombinant integral membrane protein having the amino acid sequence of SEQ ID NO: 6.

In one embodiment the described polynucleotide encodes a recombinant integral membrane protein having an amino acid sequence that is about 95% identical to that of SEQ ID NO: 7. In one embodiment the described polynucleotide encodes a recombinant integral membrane protein having an amino acid sequence that is about 96% identical to that of SEQ ID NO: 7. In one embodiment the described polynucleotide encodes a recombinant integral membrane protein having an amino acid sequence that is about 97% identical to that of SEQ ID NO: 7. In one embodiment the described polynucleotide encodes a recombinant integral membrane protein having an amino acid sequence that is about 98% identical to that of SEQ ID NO: 7. In one embodiment the described polynucleotide encodes a recombinant integral membrane protein having an amino acid sequence that is about 99% identical to that of SEQ ID NO: 7. In one embodiment the described polynucleotide encodes a recombinant integral membrane protein having the amino acid sequence of SEQ ID NO: 7.

In one embodiment the described polynucleotide encodes a recombinant integral membrane protein having an amino acid sequence that is about 95% identical to that of SEQ ID NO: 8. In one embodiment the described polynucleotide encodes a recombinant integral membrane protein having an amino acid sequence that is about 96% identical to that of SEQ ID NO: 8. In one embodiment the described polynucleotide encodes a recombinant integral membrane protein having an amino acid sequence that is about 97% identical to that of SEQ ID NO: 8. In one embodiment the described polynucleotide encodes a recombinant integral membrane protein having an amino acid sequence that is about 98% identical to that of SEQ ID NO: 8. In one embodiment the described polynucleotide encodes a recombinant integral membrane protein having an amino acid sequence that is about 99% identical to that of SEQ ID NO: 8. In one embodiment the described polynucleotide encodes a recombinant integral membrane protein having the amino acid sequence of SEQ ID NO: 8.

In some embodiments the described polynucleotides may be a segment of a plasmid, vector, phage genome, YAC, or other gene expression system. The polynucleotides described herein may be used to transform bacteria, yeast, or mammalian cells to allow for expression of the protein that the polynucleotide encodes. Accordingly, described herein are bacteria transformed with a polynucleotide encoding any one of the recombinant integral membrane proteins described herein. In some embodiments the bacterium transformed with a polynucleotide encoding any one of the recombinant integral membrane proteins described herein may be E. coli.

Methods of use for the described proteins are also provided herein. In one embodiments the described recombinant integral membrane proteins may be used in a method of obtaining a recombinant, soluble integral membrane protein having seven transmembrane domains in bacteria by: expressing in bacteria a polynucleotide encoding the recombinant integral membrane protein described herein, lysing the bacteria, and collecting a recombinant, soluble integral membrane protein having seven transmembrane domains. The expressed recombinant protein may be collected from the bacterial culture supernatant, the lysed bacterial pellet, or both. Additionally, the recombinant integral membrane protein may be collected by any number of known methodologies, such as centrifugation, affinity chromatography, size exclusion chromatography, molecular weight filtration (such as dialysis or size exclusion centrifugation).

Also provided herein are methods of identifying a ligand for any one of the recombinant integral membrane proteins described herein by contacting the recombinant integral membrane protein of interest with a compound and determining whether the two have a specific interaction. In some embodiments a specific interaction between a compound and a recombinant integral membrane protein may be identified by determining a binding affinity between the two. Alternatively, the affinity of one of the recombinant integral membrane proteins described herein for a ligand could be determined by contacting the ligand with one or more such recombinant integral membrane proteins to determine the binding affinity between the two. The affinity of the interaction may be determined by any number of mechanisms, such as calorimetry, spectral absorption, time-resolved fluorescence resonance energy transfer, or surface plasmon resonance. In some embodiments, the recombinant integral membrane protein may be attached to a surface, for example by conjugation to an antibody specific for a protein tag added to the recombinant protein, to allow one or more compounds to be tested for interaction with the protein. Similar methods could also be used to assess the structural changes the described recombinant integral membrane proteins undergo upon ligand binding. For example, in one embodiment the structure of the recombinant integral membrane protein could be assessed before and after ligand binding occurs.

The following examples are provided to describe the embodiments described herein with greater detail. They are intended to illustrate, not to limit, the embodiments.

EXAMPLE 1

Design of a Water-Soluble Variant of the Human MUR

Figure 2:
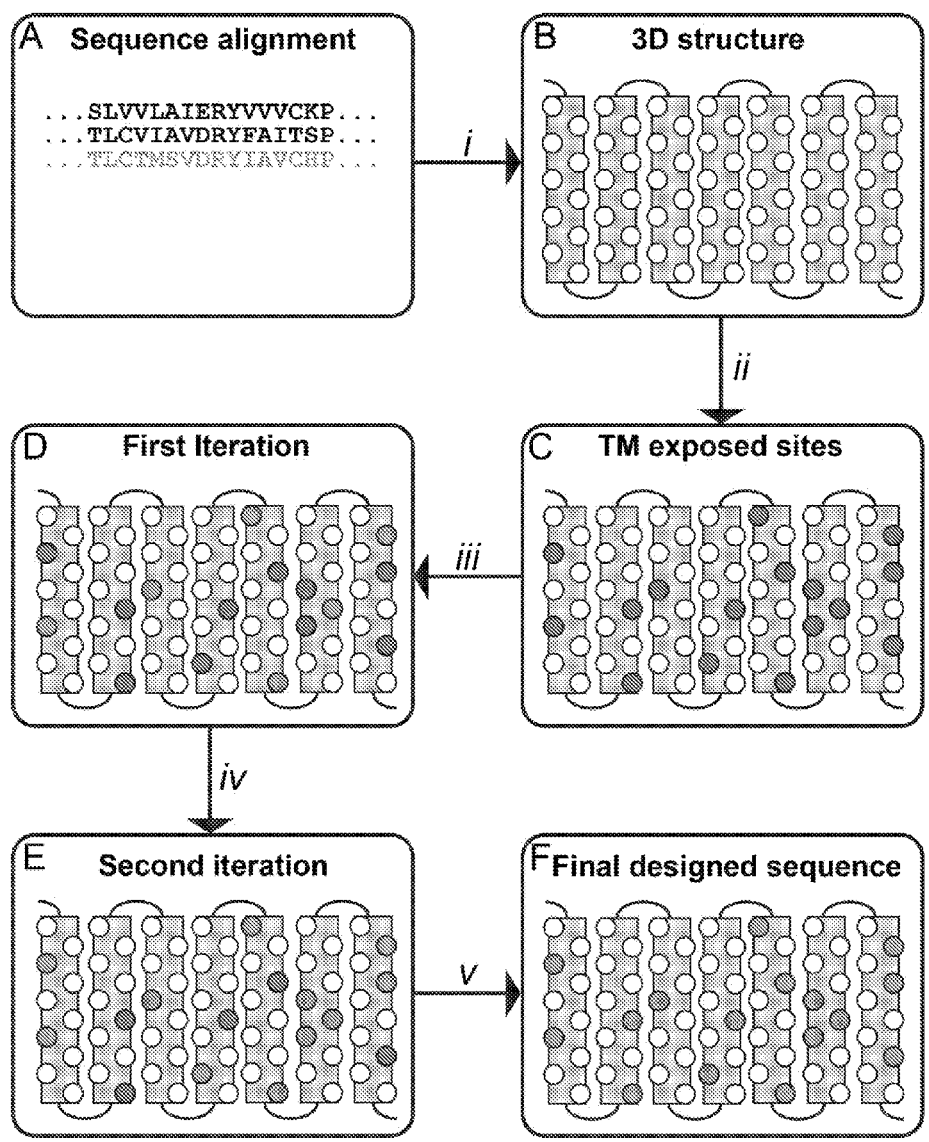
FIG. 2. Scheme of the computational design protocol. Homology modeling: Starting from the sequence alignment between known GPCR structures (bovine rhodopsin (SEQ ID NO:12) and β2 adrenergic receptor (SEQ ID NO:13)) and MUR (SEQ ID NO:14)(A), 3D structures of MUR are generated (B). Identification of exposed sites in the transmembrane portion: A representative 3D model was selected from the generated models of MUR and the transmembrane lipid-exposed positions are identified (C; dark gray dots). Computational design of selected exterior positions to generate a water-soluble variant: The selected exterior positions are targeted of the computational design calculation with the intention to increase the protein's solubility in water. By maximizing an effective entropy function subject to different energy constraints, the computational approach generates site-specific probability profiles, that is, the probability of each amino acid to be present at each of the targeted sites. The amino acid identities of the sites where the probability of a particular amino acid is strongly favored (equal or larger than 0.8) was chosen to be that of this most probable amino acid (D; light gray dots). An iterative series of such calculations were performed until the probabilities of the different positions no longer fulfill these criteria (E; light gray dots). At any remaining residues not yet specified with regard to amino acid identity, the most probable amino acid is selected (F; light gray dots).
Figure 3:
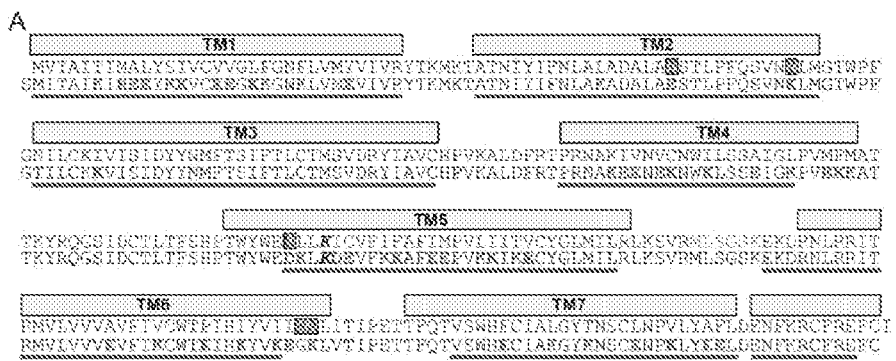
FIG. 3. (A) Sequences of the crystal structure of the mouse μ opioid receptor (PDB code 4DKL; Top (SEQ ID NO:15)) (1) and the human water-soluble variant wsMUR-TM (bottom) (SEQ ID NO:1). The murine sequence (top) corresponds to that whose structure is presented in the crystal structure of the mouse μ opioid receptor. The helical secondary structure is shown as rectangles. The gray residues in between TM5 and TM6 (MLSGSK (SEQ ID NO:10)) are absent in the crystal structure. The helical secondary structure of the wsMUR-TM model is indicated by lines under the sequence. (B) Superposition of the mouse μ opioid receptor (light gray) and the wsMUR-TM model (dark gray). (C) Rendering from the "extracellular" viewpoint of the crystal structure of mouse μ opioid receptor, where the side chain of the mutated positions in wsMUR are depicted as dark gray spheres. The majority of mutations (50 out of 55) are located at the exterior of the structure. Five remaining positions (see also residues in rectangular boxes in FIG. 3A) are also rendered: Y130, T120, A306, N232, and K305. None of these positions are in direct contact with the irreversible antagonist β-FNA based on the crystal structure, where β-FNA was covalently attached to K235.
Figure 3:
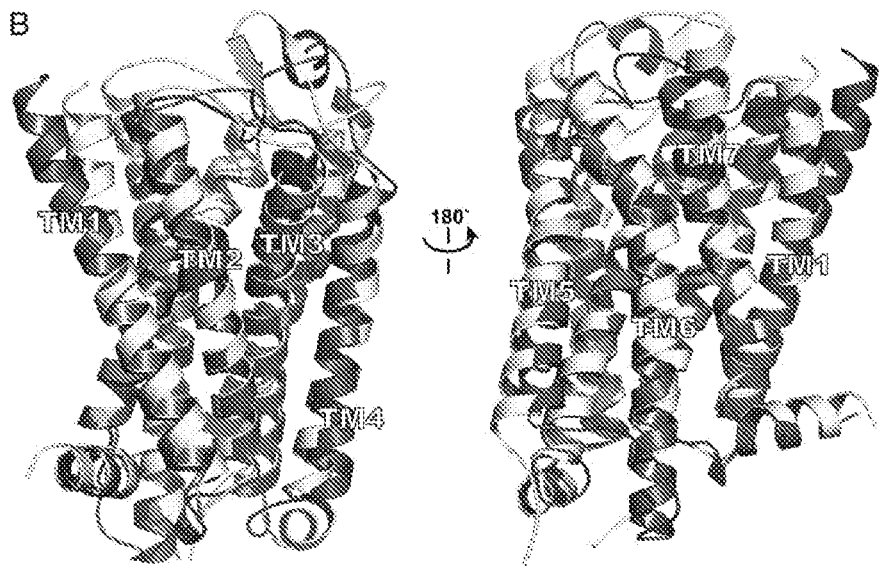
Figure 3:
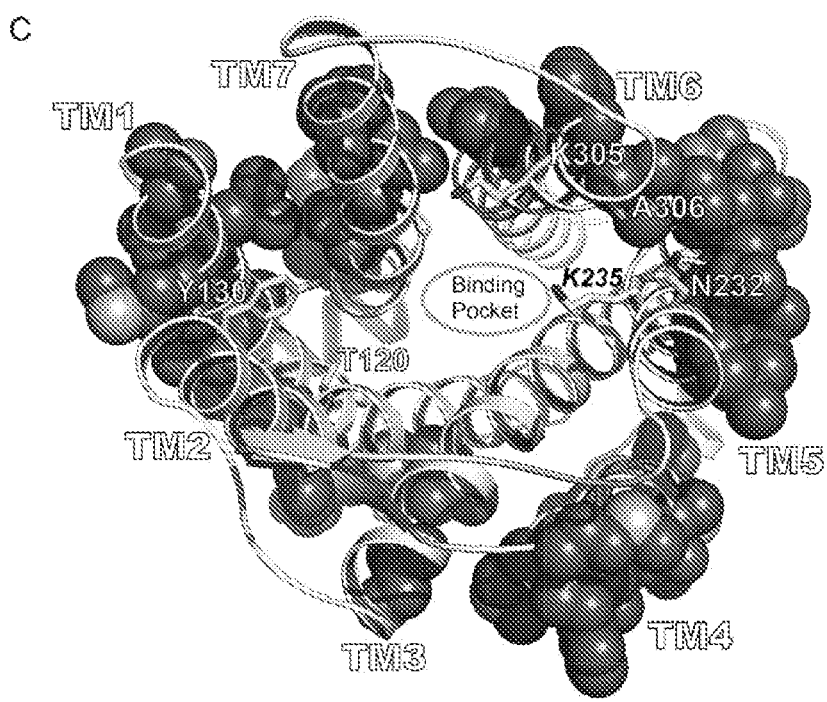
Figure 4:
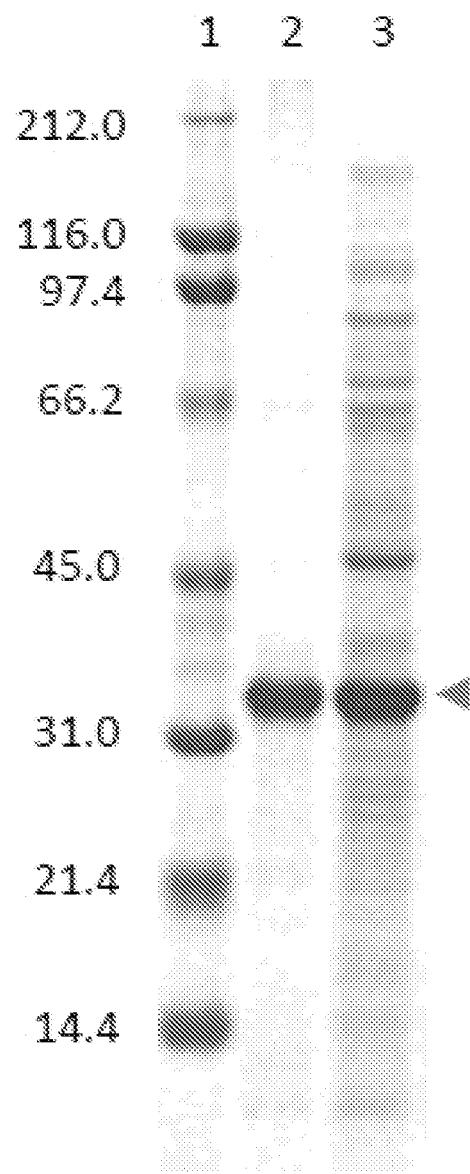
FIG. 4. Overexpression and verification of wsMUR-TM. A SDS-PAGE gel for wsMUR-TM is shown where lane 1 correspond to the molecular weight standard, lane 2 to purified wsMUR-TM and lane 3 to expressed wsMUR-TM in the crude material. The band corresponding to the wsMUR-TM appears at approximately 36 kDa.

Studies were initiated to produce a comparative model of the human MUR transmembrane domain (288 residues, 66-353) using known GPCR structures (FIG. 1A). To identify the site-specific amino acid probabilities of the target positions, a statistical entropy-based formalism was used. Energy functions to quantify sequence-structure compatibility are derived from a molecular mechanics force field. To account for solvation effects and for the tendency of different amino acids to be exposed to or sequestered from water (hydrophobicity), an energy term (herein environmental energy) based on the local density of $C_\beta$ atoms of each residue and parameterized using a large database of globular proteins was used. In this case the environmental energy term was constrained to a value expected for soluble proteins of 288 residues, the size of the segment of the human MUR encompassing the TM domain. The conformational variability of the amino acid residues is addressed using a rotamer library of side chain conformations. The site-specific probabilities of the amino acids at each of the target positions are determined by maximizing an effective entropy function subject to constraints on the two energies. These probabilities were used to identify specific sequences. Residues suitable for mutation where identified as exposed, hydrophobic amino acids. Exposure is determined via inspection of model and crystallographic structures, hydrophobic scoring of the amino acids based upon empirical energy scales, and the solvent accessible area calculated for each amino acid. This resulted in identifying 55 exterior amino acids suitable for mutation. After the residues suitable for mutations were identified, the remaining residues were fixed at their wild type identities, and their side chain conformations were allowed to vary to accommodate designed mutations. All amino acids but proline and cysteine were permitted at each of the identified variable positions. A hydrophobicity scoring function (environmental energy) was applied and selected to have a value consistent with that of a globular water-soluble protein having 288 amino acids. Identification of sequence proceeded iteratively (FIG. 2). In all, 55 exterior transmembrane residues were selected for the computational redesign. A first calculation using the method described above to calculate the site-specific probabilities of the amino acids at each of 55 variable residues identified 31 positions where the probability of the selected amino acid exceeded 0.8; each such residue was mutated to this most probable amino acid, yielding the following mutations: $A75E^{1.37}$, $S78K^{1.40}$, $I79K^{1.41}$, $V83E^{1.45}$, $F89K^{1.51}$, $Y93E^{1.55}$, $T120E^{2.54}$, $K187K^{4.43}$, $I188E^{4.44}$, $V191E^{4.47}$, $C192K^{4.48}$, $A199E^{4.55}$, $L202K^{4.58}$, $M205E^{4.61}$, $N232D^{5.36}$, $L233K^{5.37}$, $I240K^{5.44}$, $F241K^{5.45}$, $I244E^{5.48}$, $M245E^{5.49}$, $L248K^{5.52}$, $V252E^{5.56}$, $A289E^{6.42}$, $V293K^{6.46}$, $P297E^{6.50}$, $I300K^{6.53}$, $I303K^{6.56}$, $I304E^{6.57}$, $A306K^{6.59}$, $L326K^{7.41}$, and $V336K^{7.31}$. The superscript notation is consistent with the Ballesteros and Weinstein indexing system: (number of the transmembrane helix).(residue number relative to most conserved residue in transmembrane helix, which is assigned position 50). These residue identities were fixed in subsequent calculations. Similarly, second and third calculations specified one ($V82E^{1.44}$) and two ($T72K^{1.34}$ and $L333E^{7.48}$), respectively, additional positions with the same probability threshold. Using the results of a fourth calculation, the most probable amino acid was selected at the remaining 21 positions, yielding a sequence and model structure for wsMUR-TM as presented in FIG. 1B. The designed sequence is presented in FIG. 3A. The recent structure of the closely related murine MUR provides an opportunity to evaluate the structure and the location of the mutated positions in wsMUR-TM. The human and mouse receptors have 94% sequence identity. The model of the human MUR and the murine crystal structure superimpose well (FIG. 3B), particularly with regard to the transmembrane helices. Only five positions in wsMUR-TM were not located in the exterior of the murine structure (T120E, Y130K, N232D, K305G, and A306K) and could in principle affect ligand binding (FIG. 3C). In the murine structure, however, these five positions residues were not among the residues that directly contact beta-Funaltrexamine (β-FNA), an irreversible antagonist of the receptor.

Other attempts to produce a water-soluble MUR protein were not successful. While some of these constructs did not express in bacteria, as was the case with the native protein, those that did express were not functional, including the native MUR protein. In all, wsMUR-TM was only one of 11 recombinant MUR constructs to have increased water solubility that could be expressed in bacteria and also bind to a native MUR ligand with comparable affinity to the native protein. Following the production of wsMUR-TM; however, several other variants were produced that could be expressed in *E. coli* and also retained functionality (described in Example 5).

EXAMPLE 2

Expression and Purification of wsMUR-TM

A synthetic cDNA encoding the transmembrane-only water-soluble MUR variant (wsMUR-TM) was produced by DNA2.0 Inc. (Menlo Park, Calif.). The sequences were subcloned between the NdeI and XhoI restriction sites of the expression plasmid pET-28b(+) (EMD/Novagen®). *E. coli* BL21(DE3) cells (EMD/Novagen®) were used for expression. Cells were grown in shake flasks with Lysogeny broth medium with 30 μg/mL kanamycin to an optical density (OD) of 1.0, induced with 1 mM Isopropyl β-D-1-thiogalactopyranoside (IPTG) for 3 hours at 37° C., then pelleted by centrifugation. Cell pellets were stored at 20° C. until purification. For solubility testing, 1 OD aliquots of cells were pelleted in microcentrifuge tubes, suspended in 150 μL of TE (50 mM Tris-HCl, 1 mM EDTA, pH=8.0), then shaken with 0.3 g of glass beads (0.1 mm diameter) for 5 min. Aliquots of the resulting lysates were spun in a microcentrifuge for 1 min. Aliquots of total lysate, or the supernatant and pellet fractions after centrifugation, were analyzed on reducing sodium dodecyl sulfate (SDS) gels.

Frozen cells from 250 mL of fermentation (500-550 ODs) were thawed, and then suspended in 33.5 mL of 50 mM Tris-HCl, 1 M urea, pH=8.0. Once the pellet was fully resuspended, EDTA was added to 1 mM, Triton™ X-100 to 1%, and hen egg lysozyme to 1 μg per OD of cells, in a total volume of 37 mL. After the slurry was incubated for 20 min at room temperature (RT), MgCl2 was added to 3 mM, followed by 100 units of benzonase. The suspension was swirled, incubated another 5 min at RT, and then spun in an Oak Ridge tube at 10,000 rpm for 20 min at 20° C. in an SS-34 rotor (ravg=6.98 cm, rmax=10.70 cm).

The resulting pellet was resuspended into 35 mL of 50 mM Tris-HCl, 1 M urea, pH=8.0. Triton™ X-100 (1.5 mL of a 25% solution) and 2-mercaptoethanol (2-ME) was added to 40 mM. The tube was inverted several times, and then spun as above.

The following steps were designed to resemble those that had been used to dissolve and purify recombinant forms of native μ opioid receptor. The pellet from the above washes was resuspended into 5 mL of buffer phosphate Tris buffer (100 mM phosphate, 10 mM Tris, adjusted to pH=8.0 with NaOH) and dispersed by drawing through a pipet followed by a 25 gauge needle. The volume was then raised to 37 mL by addition of phosphate Tris buffer, and 2-ME was then added to 40 mM. The tube was inverted to mix, then spun as above.

The resulting pellet was dispersed into 36 mL of PT as described above. The suspension was then mixed with an equal volume of phosphate Tris buffer containing 0.2% SDS and 10 mM 2-ME. The suspension was rocked until it became almost clear (60-90 min) The suspension was then poured into two 38 mL Oak Ridge tubes. These were spun tube at 12,000 rpm for 20 minutes at 20° C. in an SS-34 rotor.

Since an initial exposure to 0.1% SDS was required during purification, the purified wsMUR-TM in solution may still contain small amounts of SDS due to the difficulty of removing SDS from proteins. In order to avoid protein aggregation, 0.01% of SDS was utilized in the final buffer solutions for functional assays. Using binding and crystallographic studies, it has been shown that such small amounts of SDS do not disrupt the tertiary structure and/or the ligand binding capabilities of some proteins. Conversely, a much higher concentration of SDS (0.1%) and other anionic detergents are required for the "solubilization" of the native human MUR.

Attempts to express the native full-length human MUR in *E. coli* were unsuccessful presumably due to the protein's toxicity. In contrast, wsMUR-TM expressed well and was isolated with high purity using affinity chromatography (FIG. 4). The yield was ~20 mg/L of shake flask culture. An initial exposure to ~0.1% sodium dodecyl sulfate (SDS) was required to purify the receptors. After dialysis to remove non-bound SDS, the purified variant were soluble at 6 mg/mL in buffer solution (130 mM NaCl, 20 mM NaHPO4, pH=7.0).

EXAMPLE 3

Protein Structure Characterization and Thermostability

The secondary structure of the water-soluble variant was determined through circular dichroism (CD). Circular dichroism (CD) spectra were recorded by using CD Spectrometer (Chirascan, AppliedPhotophysics Limited, Leatherhead, United Kingdom) with a scan speed of 1 nm/s and 1 mm path length. Corresponding blanks were used for calibration for each assay and subtracted from raw data. Two data sets were recorded and averaged to increase the signal-to-noise ratio. The CDNN CD spectra deconvolution software was utilized to determine the secondary structure content of the proteins. CD spectroscopy for wsMUR-TM at different temperatures were recorded with 6 μM of the receptor in buffer (5 mM sodium phosphate, pH=7.0) from 10° C. to 90° C. in increments of 2° C. per min. Absorbance was maintained lower than 1.0 to ensure sufficient light transmission. The temperature-dependence curve was plotted using GraphPad Prism® (version 5, GraphPad Software, Inc. La Jolla).

The CD spectra indicated predominantly helical structures with a helical secondary structure content of ~48% (estimations based on the molar ellipticity over the range 205 to 260 nm). The comparison of the helical content with that of the native human MUR expressed in yeast system in the presence of high concentration of detergent (0.1% SDS) is presented in Table 1.

TABLE 1

Helical content comparison for the native and engineered receptors

Figure 5:
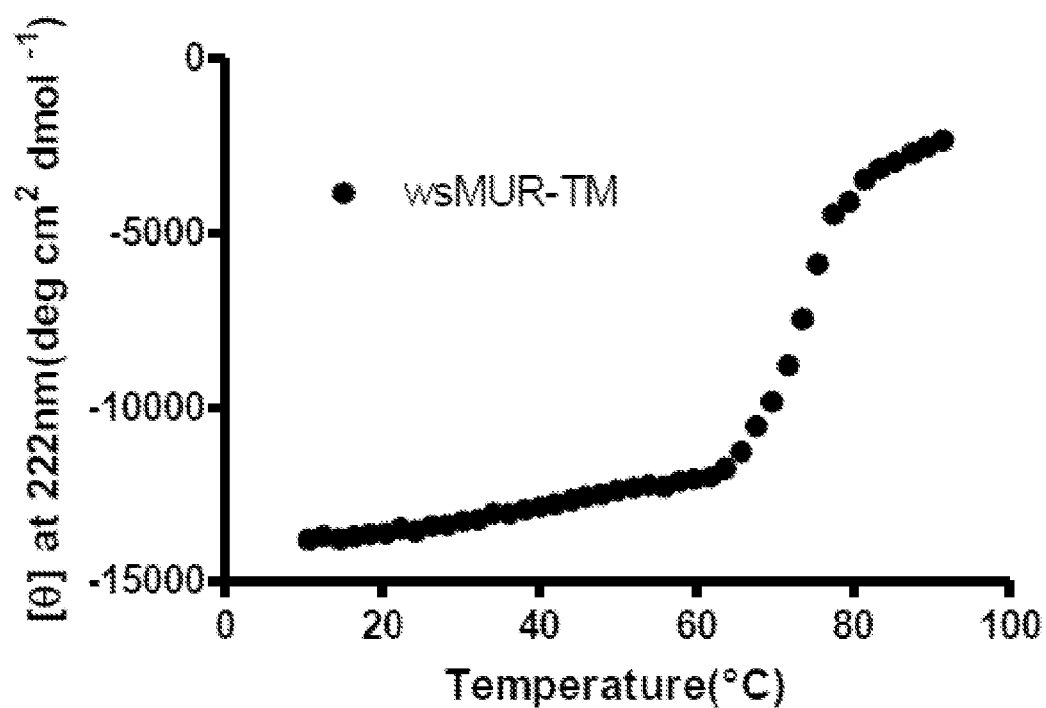
FIG. 5. Mean residue ellipticity at 222 nm of wsMUR-TM in buffer solution (5 mM sodium phosphate, pH=7.0) as a function of temperature, from 10 to 90° C. The spectrum of wsMUR-TM showed significant change near 62° C. and an almost complete loss in molar ellipticity at 90° C.
Figure 6:
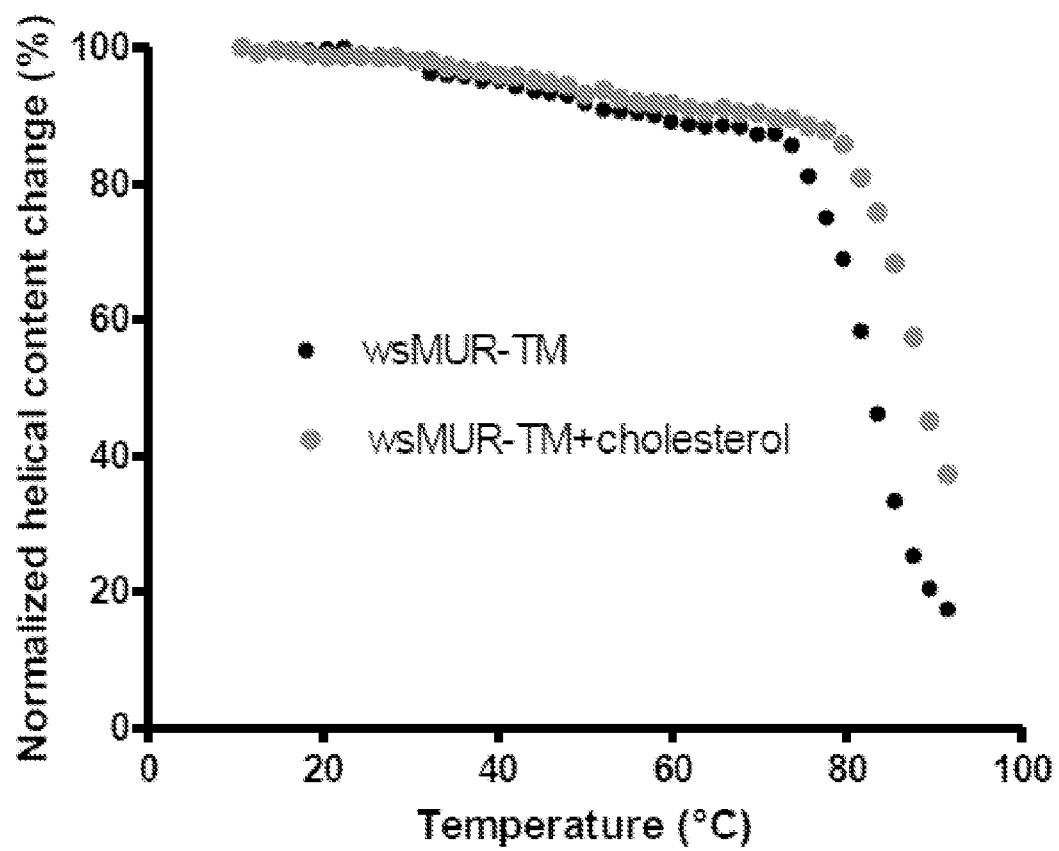
FIG. 6. Molar circular dichroism (CD) derived percentage of the original helical content (determined at 222 nm) of wsMUR-TM in the absence (inner-most doted plot) and the presence (outer-most doted plot) of cholesterol in buffer solution (5 mM sodium phosphate, 0.01% SDS, pH=7.0) as functions of the temperature. The addition of cholesterol stabilized the wsMUR-TM as indicated by the rightward shift of the thermostability curve.

| 205-260 nm | wsMUR-TM (pH 7.0 in NaHPO$_4$) | Native MUR (pH 7.0 + 0.1% SDS) |
|---|---|---|
| Helix | 48.0% | 40.6% |
| Turn | 14.6% | 18.9% |
| Others | 37.4% | 40.5% | wsMUR-TM: transmembrane-only water-soluble human mu receptor variant;
MUR: human μ receptor As monitored by CD, wsMUR-TM started to lose ellipticity significantly near 62° C. and was almost fully unfolded at 90° C. (FIG. 5). The stability of wsMUR-TM was also investigated upon addition of cholesterol, which has been found to modulate the stability of several GPCRs. The inclusion of cholesterol caused a shift of the melting point from 82.9° C. to 89.3° C., suggesting that it may stabilize the helical structure of wsMUR-TM (FIG. 6).

CD and intrinsic tryptophan fluorescence were used to probe disulfide bond formation in the water-soluble variant. The structure of wsMUR-TM was monitored with increasing concentrations of urea and the reducing agent 2-mercaptoethanol (2-ME). After addition of urea, the molar ellipticity at 222 nm and the intensity of the intrinsic tryptophan fluorescence of wsMUR-TM decreased. Even in 8 M urea, the protein retains some helical structure (Table 2). Upon addition of 2-ME, both the molar ellipticity and fluorescence further decreased, becoming more pronounced at the higher concentration of the reducing agent (200 mM). Thus the presence of an intramolecular disulfide bond is corroborated in the case of wsMUR-TM.

TABLE 2

Effects of denaturant and reducing agent on the wsMUR-TM

| | None | Urea (8M) | Urea (8M) 2-ME (25 mM) | Urea (8M) 2-ME (200 mM) |
|---|---|---|---|---|
| Molar Ellipticity (%; 222 nm) | 100.0 | 40.0 | 25.1 | 0.0 |
| Fluorescence Peak Intensity (%; 300-350 nm) | 100.0 | 28.4 | 23.9 | 4.5 | wsMUR-TM: transmembrane-only water-soluble human μ receptor variant;
Values are normalized to the condition without denaturant or reducing agent (None).
2-ME: 2-mercaptoethanol.

Intrinsic tryptophan fluorescence was used to provide qualitative information of the conformations adopted by the water-soluble receptors; wsMUR-TM contains just six tryptophan residues (W135$^{2.69}$, W194$^{4.50}$, W228$^{EC2}$, W230$^{EC2}$, W295$^{6.48}$, and W320$^{7.35}$). Of particular interest are the tryptophan residues located in the partially buried transmembrane locations of the model structure (positions 194, 295, and 320). The fluorescence associated with these residues is expected to be sensitive to the local hydrophobic environment and overall folding of the protein. The observed decrease in the tryptophan fluorescence and the red shift in the emission with increasing denaturant (urea) concentration suggest that at least some of these tryptophan residues are located in the interior of the protein.

The decrease of the tryptophan fluorescence under denaturing conditions and in the presence of 2-ME is consistent with the changes in CD spectra observed under similar conditions. The requirement of the reducing agent to fully denature and unfold the protein indicates the relevance of an intramolecular disulfide bond in stabilizing the receptor structure. Although these observations suggest the presence of a disulfide bond, they do not specify which bond is formed given the existence of 11 cysteine residues in wsMUR-TM. However, the CD and ligand-binding studies are consistent with the adoption of the proper protein tertiary structure and by extension with the formation of the correct disulfide bond.

EXAMPLE 4

Ligand Binding Properties of the wsMUR-TM

Figure 7:
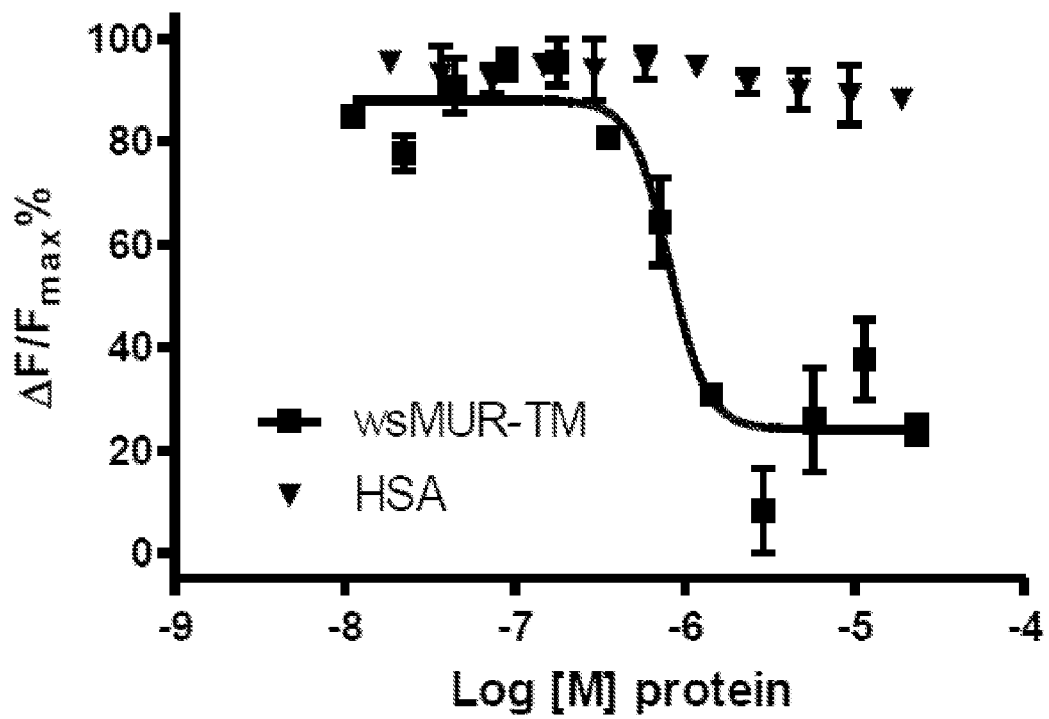
FIG. 7. Binding competition assay between the human μ opioid receptor expressed in HEK293 cells and the μ opioid water-soluble variants Inhibition of the native μ opioid receptor constitutive signal in the presence of increasing concentrations of wsMUR-FL (dots, $IC_{50}=8.4\times10^{-7}$ M, $R^2=0.9306$) or wsMUR-TM (squares, $IC_{50}=8.6\times10^{-7}$M, $R^2=0.9067$) in sodium phosphate buffer. Data for the negative control is also included, HSA (inverted triangles). Data is used to calculate HTRF ratios, and represent the mean±standard error of mean of quadruplicates. ΔF is used for the comparison of different runs of the same assay which reflects the signal to background of the assay. $\Delta F=[(\text{Ratio}_{sample}-\text{Ratio}_{backgroud})/\text{Ratio}_{backgroud}]$ (%).

A recently developed methodology which uses a fluorescently labeled ligand and the native MUR was used to investigate the ligand-binding capabilities of the water-soluble receptors. Naltrexone binding was monitored using a competitive TR-FRET (time-resolved fluorescence resonance energy transfer) based assay with fluorescently labeled wild type MUR and a naltrexone-derived antagonist. The ratio of fluorescence emission at 665 nm and 620 nm decreased in a dose-dependent manner with increasing concentrations of wsMUR-TM. The determined $K_d$ values for naltrexone were 65±1.8 nM (wsMUR-TM) (FIG. 7). As a negative control, human serum albumin (HSA, a soluble helical protein), rather than a water-soluble variant, was introduced with no significant change in the fluorescence ratio upon HSA addition.

This binding assay has been applied to study several GPCRs and particularly MUR, where the $K_i$ values for the morphinan opioids naloxone and naltrindole were estimated (5.1 nM and 8.1 nM for naloxone and naltrindole, respectively) and found to be in agreement with values obtained using other techniques, wsMUR-TM competes with native MUR expressed in HEK293 cells for the potent opioid antagonist naltrexone. This study demonstrates that the wsMUR-TM can compete with the native MUR for the fluorescent antagonist with binding affinities in nM range. The HSA (negative control) results indicate that the interaction of the water-soluble variant with naltrexone is selective and specific.

EXAMPLE 5

Additional MUR Constructs

Figure 8:
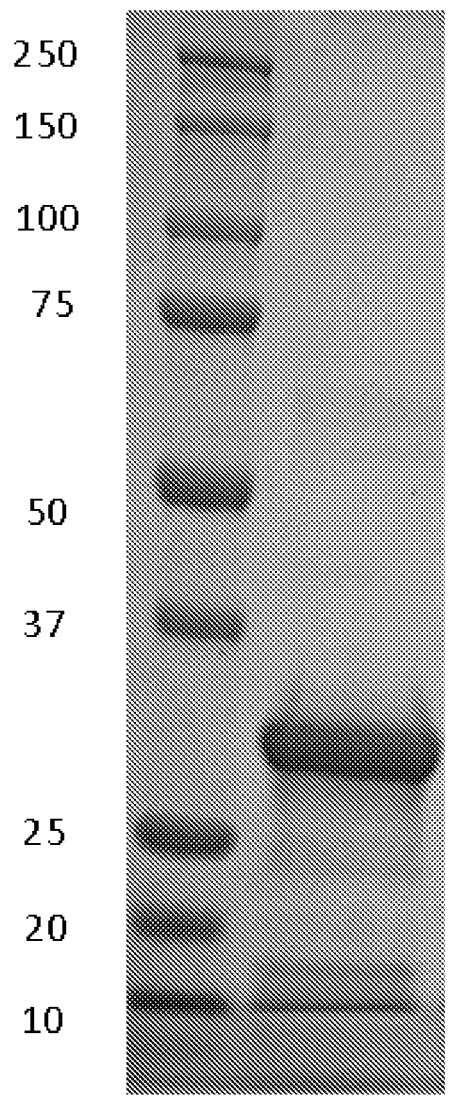
FIG. 8. Expression and purification of wsMUR-TM (SEQ ID NO: 2).
Figure 9:
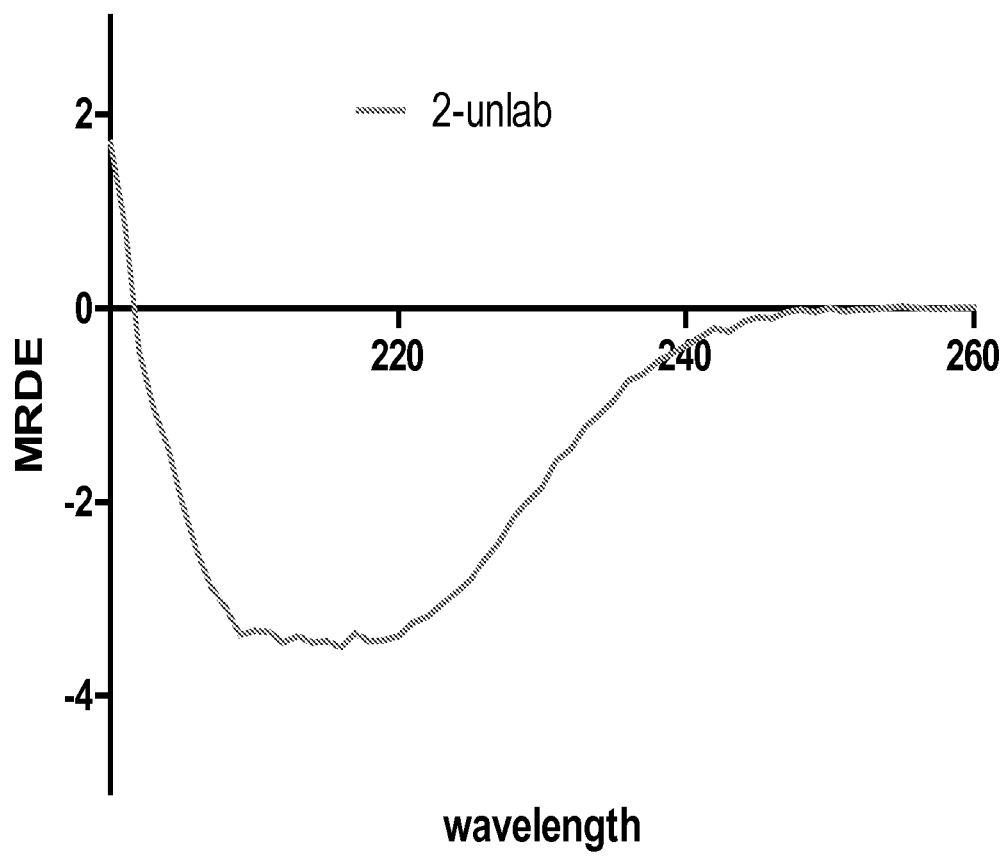
FIG. 9. The secondary structure of wsMUR as indicated by CD spectra analysis.
Figure 10:
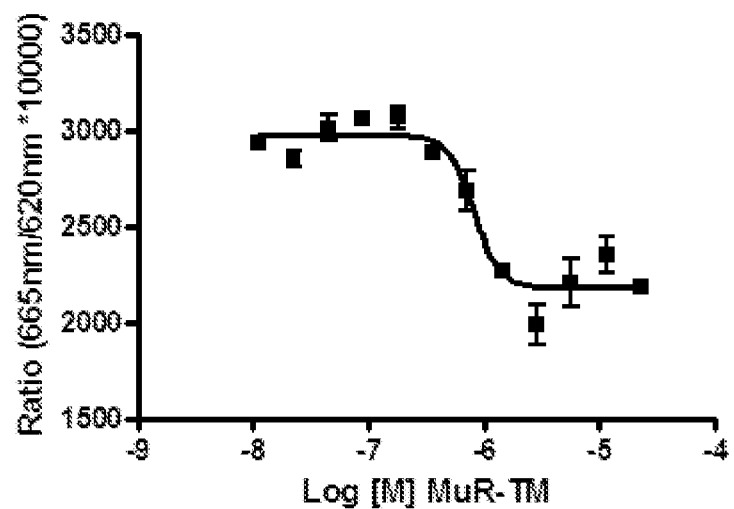
FIG. 10. The specific interaction of naltrexone with the wsMUR, similar to that indicated in FIG. 7.
Figure 11:
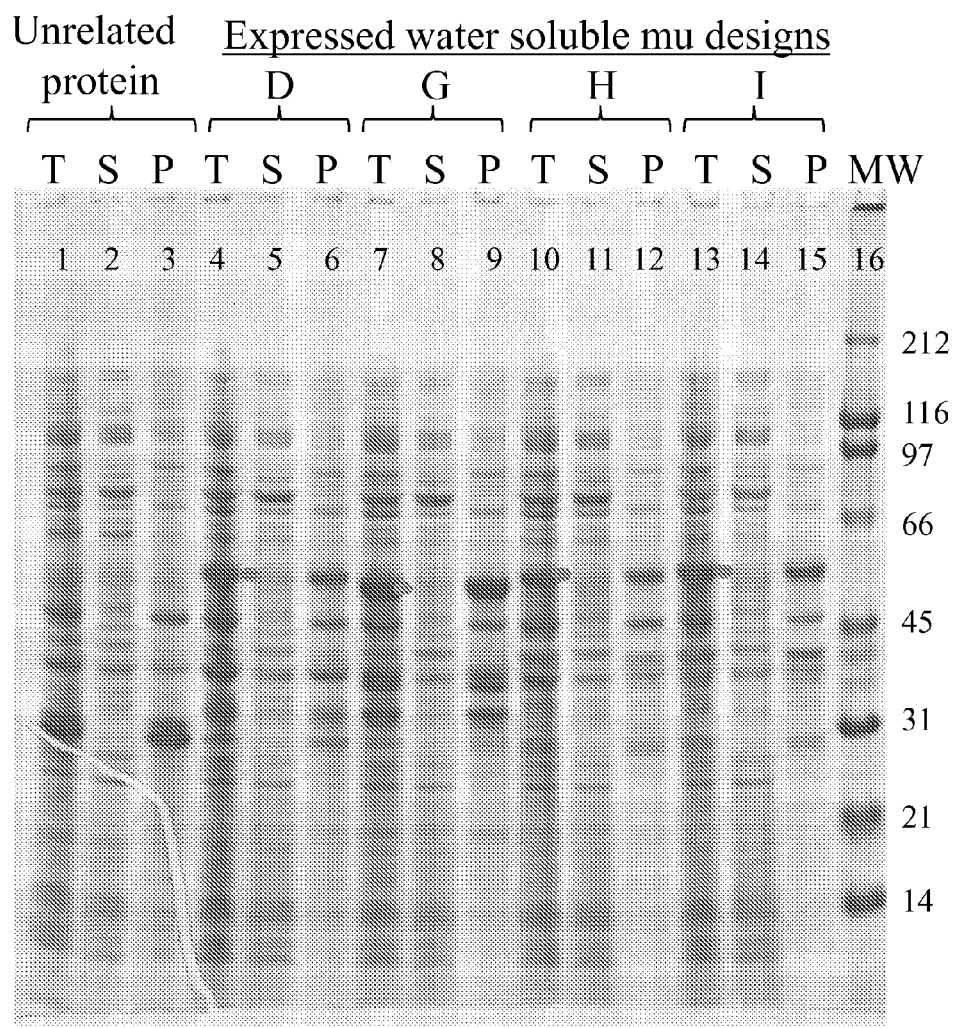
FIG. 11. Expression of 4 different versions of the wsMURs (SEQ ID NOs: 3-6). All 4 version of the receptors are expressed well in *E. Coli* and were purified successfully using affinity chromatography.
Figure 12:
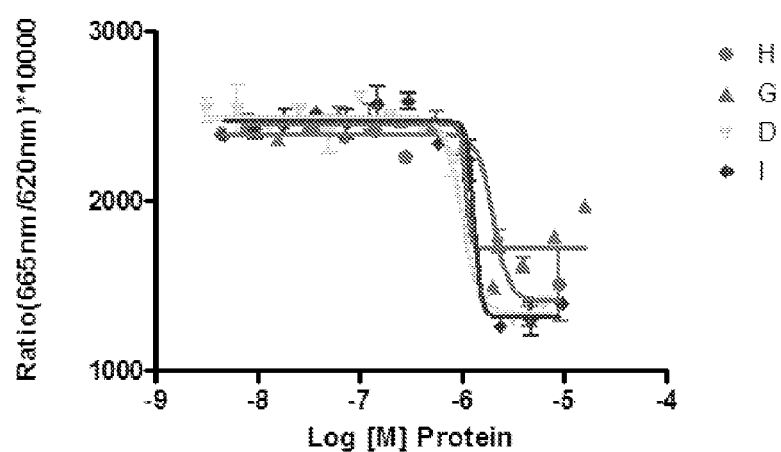
FIG. 12. Four versions of the wsMUR demonstrate comparable affinities with naltrexone by using the methodology described for FIG. 7.

Constructs having unique sequences, but similar properties to the wsMUR-TM construct were also produced and analysed as described above. One such construct is a second wsMUR recombinant protein (wsMUR-TM+7mut—SEQ ID NO: 2). Studies performed to characterize wsMUR-TM+7mut demonstrate its production and isolation using bacterial expression (FIG. 8), its alpha-helical nature as measure by CD (FIG. 9), and binding activity was also observed for related MUR constructs wsMUR-TM+7mut (FIG. 10). Similar characteristics were observed for the MUR constructs G-min (SEQ ID NO: 3), H-min (SEQ ID NO: 4), I-min (SEQ ID NO: 5), and D-min (SEQ ID NO: 7) (see figures FIGS. 11 and 12).

EXAMPLE 6

Figure 13:
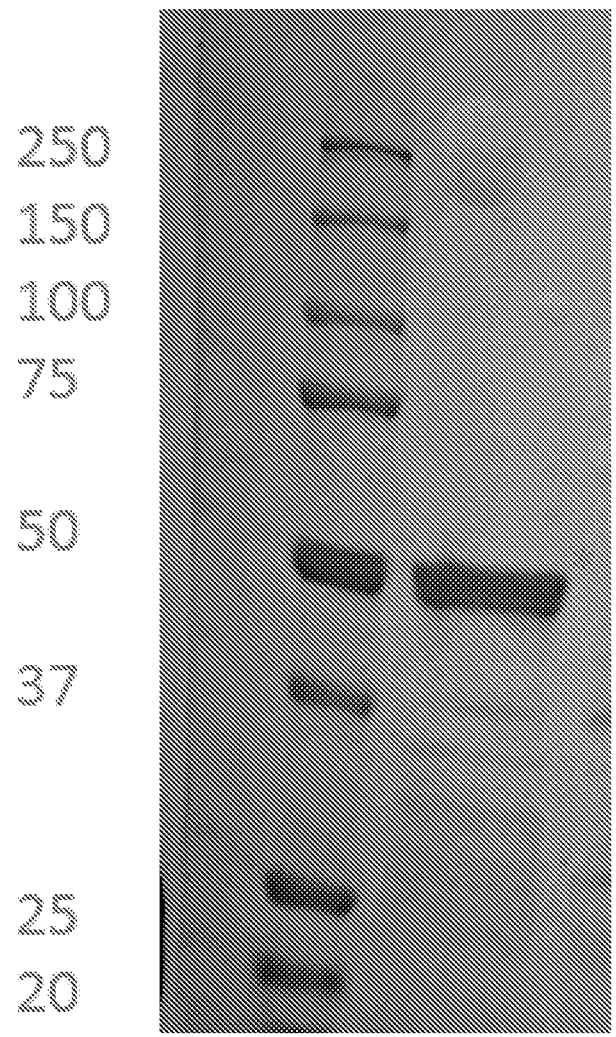
FIG. 13. Expression and purification of a water-soluble variant of the beta-adrenergic receptor.
Figure 14:
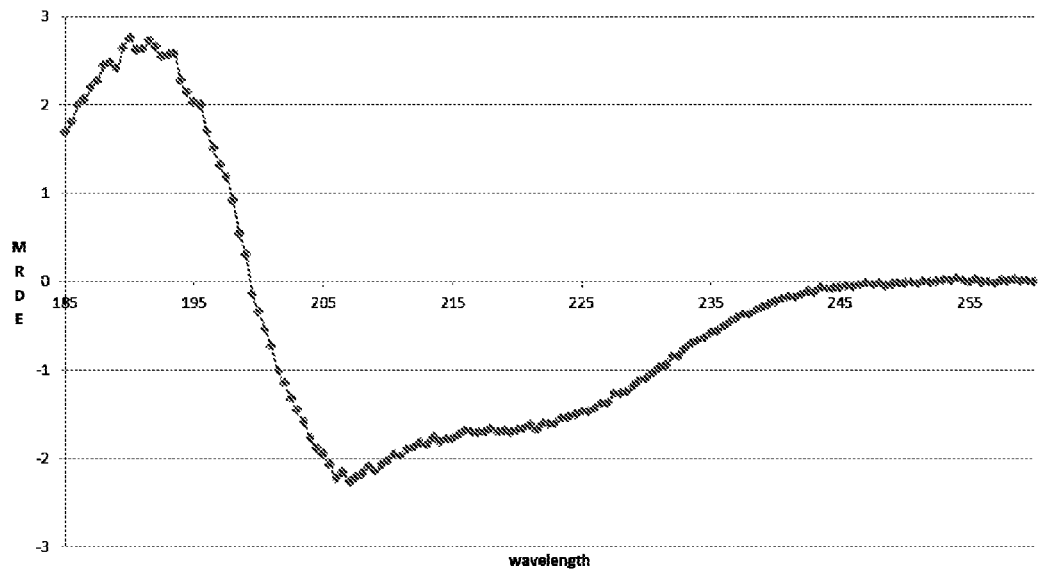
FIG. 14. The secondary structure of the water soluble beta-adrenergic receptor as indicated by the CD spectra analysis.

Production and Isolation of a Water-Soluble Human Beta$_2$ Adrenergic Receptor Studies were conducted to engineer and generate a more water soluble human β$_2$ adrenergic receptor (BAD). After analyzing the native protein sequence, as described above for MUR, amino acid sequence changes were made to cause the engineered BAR to be less hydrophobic. Two recombinant BAR sequences were designed (SEQ ID NOs: 7 and 8). To assess expression and isolation from bacteria, E. coli were transformed with a construct encoding SEQ ID NO: 8 (BAD4), cultured and then lysed. BAD4 was identified on a western blot following purification from the bacterial cell lysate (FIG. 13). The isolated protein was also assessed for helical structural content by CD spectroscopy and was shown to have a spectral profile consistent with high alpha-helical content (FIG. 14).

What is claimed:

1. A recombinant integral membrane protein derived from a native protein and having seven transmembrane domains, the seven transmembrane domains comprising at least 4 transmembrane domains each having at least 3 amino acid mutations compared to the native protein that decrease the overall hydrophobicity of the recombinant integral membrane protein relative to that of the native protein, wherein the native protein is a human mu opioid receptor, and wherein the recombinant integral membrane protein assumes an active conformation when bound to a native ligand.

2. The recombinant integral membrane protein of claim 1, comprising at least 5 transmembrane domains each having at least 3 amino acid mutations that decrease the overall hydrophobicity of the recombinant integral membrane protein relative to that of the native protein.

3. The recombinant integral membrane protein of claim 1, wherein said recombinant integral membrane protein is characterized as being a G-protein-coupled receptor (GPCR).

4. The recombinant integral membrane protein of claim 1, wherein the recombinant integral membrane protein has an amino acid sequence that is at least 95% identical to SEQ ID NO: 1.

5. The recombinant integral membrane protein of claim 1, wherein the recombinant integral membrane protein is water soluble.

6. The recombinant integral membrane protein of claim 1, wherein the recombinant integral membrane protein further comprises an epitope tag.

7. The recombinant integral membrane protein of claim 6, wherein the epitope tag comprises 5 consecutive histidine amino acids.

8. A polynucleotide encoding a recombinant integral membrane protein derived from a native protein and having seven transmembrane domains, comprising 4 transmembrane domains each having at least 3 amino acid mutations compared to the native protein that decrease the overall hydrophobicity of the recombinant integral membrane protein relative to that of the native protein,
   wherein the native protein is a human mu opioid receptor, and
   wherein the recombinant integral membrane protein assumes an active conformation when bound to a native ligand.

9. The polynucleotide of claim 8, wherein the polynucleotide resides in a bacterium.

10. The polynucleotide of claim 9, wherein said bacterium is *E. coli*.

11. A method of identifying a binding compound for a recombinant integral membrane protein derived from a native protein and having seven transmembrane domains, comprising 4 transmembrane domains each having at least 3 amino acid mutations compared to the native protein that decrease the overall hydrophobicity of the recombinant integral membrane protein relative to that of the native protein, comprising:
   contacting said recombinant integral membrane protein with a compound, and
   determining the affinity of said recombinant integral membrane protein for said compound,
   wherein the native protein is a human mu opioid receptor, and
   wherein the recombinant integral membrane protein assumes an active conformation when bound to a native ligand.

12. The method of claim 11, wherein the recombinant integral membrane protein is attached to a surface.

13. The method of claim 11, wherein the affinity of the compound for the recombinant integral membrane protein is measured by calorimetry, spectral absorption, time-resolved fluorescence resonance energy transfer, or surface plasmon resonance.

14. The method of claim 11, further comprising obtaining the recombinant, soluble integral membrane protein by expressing in bacteria a polynucleotide encoding the recombinant integral membrane protein and collecting the recombinant, soluble integral membrane protein.

15. The method of claim 11, wherein said compound comprises one or more ligands, one or more proteins, or both.

16. The method of claim 15, wherein the compound comprises one or more ligands, and further comprising contacting the compound with the one or more recombinant integral membrane proteins and assessing the affinities of said recombinant integral membrane proteins for said compound.

17. The method of claim 11, further comprising assessing the structure of the compound.

18. The method of claim 15, wherein the compound comprises one or more proteins, and further comprising contacting the compound with the one or more recombinant integral membrane proteins and assessing the affinities of said proteins for said compound.

* * * * *

UNITED STATES PATENT AND TRADEMARK OFFICE
CERTIFICATE OF CORRECTION

PATENT NO. : 9,670,264 B2
APPLICATION NO. : 14/786578
DATED : June 6, 2017
INVENTOR(S) : Renyu Liu et al.

Page 1 of 1

It is certified that error appears in the above-identified patent and that said Letters Patent is hereby corrected as shown below:

In the Specification

Column 1
Lines 17-22, delete "The subject matter disclosed herein was made with government support under K08-GM-093115-01 awarded by the National Institutes of Health, and DMR-0425780, DMR08-32802 and DMR-1120901, which were awarded by the National Science Foundation. The Government has certain rights in the herein disclosed subject matter." and insert --This invention was made with government support under Grant Numbers GM093115, DMR0425780, DMR0832802 and DMR1120901 awarded by the National Science Foundation. The government has certain rights in the invention.--

Signed and Sealed this
Nineteenth Day of February, 2019

Andrei Iancu
*Director of the United States Patent and Trademark Office*